United States Patent
Saxell et al.

(10) Patent No.: US 9,173,391 B2
(45) Date of Patent: Nov. 3, 2015

(54) CRYSTALLINE COMPLEXES OF 4-HYDROXY BENZOIC ACID AND SELECTED PESTICIDES

(75) Inventors: Heidi Emilia Saxell, Carlsberg (DE); Rafel Israels, Cologne (DE); Ansgar Schaefer, Karlsruhe (DE); Matthias Bratz, Maxdorf (DE); Hans Wolfgang Hoeffken, Ludwigshafen (DE); Ingo Brode, Ludwigshafen (DE); Elisa Nauha, Jyvaeskylae (FI); Maija Nissinen, Jyvaeskylae (FI)

(73) Assignee: BASF SE, Ludwigshafen (DE)

( * ) Notice: Subject to any disclaimer, the term of this patent is extended or adjusted under 35 U.S.C. 154(b) by 7 days.

(21) Appl. No.: 13/505,896

(22) PCT Filed: Oct. 28, 2010

(86) PCT No.: PCT/EP2010/066401
§ 371 (c)(1), (2), (4) Date: May 3, 2012

(87) PCT Pub. No.: WO2011/054741
PCT Pub. Date: May 12, 2011

(65) Prior Publication Data
US 2012/0220463 A1     Aug. 30, 2012

(30) Foreign Application Priority Data
Nov. 6, 2009 (EP) .................................. 09175247

(51) Int. Cl.
| | | |
|---|---|---|
| *A01N 37/10* | (2006.01) | |
| *A01N 43/40* | (2006.01) | |
| *A01N 43/653* | (2006.01) | |
| *A01N 43/56* | (2006.01) | |
| *C07D 401/04* | (2006.01) | |
| *A01P 21/00* | (2006.01) | |
| *C07D 213/61* | (2006.01) | |
| *C07D 249/08* | (2006.01) | |
| *C07D 405/06* | (2006.01) | |
| *C07D 231/22* | (2006.01) | |
| *A01P 3/00* | (2006.01) | |
| *A01N 43/50* | (2006.01) | |
| *C07D 213/82* | (2006.01) | |
| *A01N 25/00* | (2006.01) | |

(52) U.S. Cl.
CPC ...................................... *A01N 25/00* (2013.01)

(58) Field of Classification Search
None
See application file for complete search history.

(56) References Cited

U.S. PATENT DOCUMENTS

| | | | |
|---|---|---|---|
| 7,135,571 B2 | 11/2006 | Henton et al. | |
| 7,138,524 B2 | 11/2006 | McCarty et al. | |
| 8,212,054 B2 | 7/2012 | Krapp et al. | |
| 2006/0154825 A1 | 7/2006 | Mayer et al. | |
| 2007/0299033 A1* | 12/2007 | McMahon et al. | 514/50 |
| 2008/0234350 A1 | 9/2008 | Ziegler et al. | |

FOREIGN PATENT DOCUMENTS

| | | | |
|---|---|---|---|
| WO | WO 2004/072039 | 8/2004 | |
| WO | WO 2006/136357 | 12/2006 | |
| WO | WO 2008/096005 | 8/2008 | |
| WO | WO2008/106151 | * 9/2008 | ........... A61K 31/497 |
| WO | WO2008117037 | * 10/2008 | ........... C07D 405/06 |
| WO | WO2009/140466 | * 11/2009 | ........... C07D 413/12 |
| WO | WO 2014/060449 | 4/2014 | |

OTHER PUBLICATIONS

International Search Report completed May 3, 2011, in International Application No. PCT/EP2010/066401, filed Oct. 28, 2010.
International Preliminary Report on Patentability dated May 8, 2012, from corresponding International Application No. PCT/EP2010/066401, filed Oct. 28, 2010.
Viertelhaus, Martin et al., "Piracetam Co-Crystals with OH-Group Functionalized Carboxylic Acids", Crystal Growth & Design, 2009, p. 2220-2228, vol. 9, No. 5.

* cited by examiner

*Primary Examiner* — Mina Haghighatian
*Assistant Examiner* — Erin Hirt
(74) *Attorney, Agent, or Firm* — Brinks Gilson & Lione

(57) ABSTRACT

The present invention relates to crystalline complexes of 4-hydroxy benzoic acid and selected pesticides. It also relates to agriculturally useful compositions of the complexes.

18 Claims, 12 Drawing Sheets

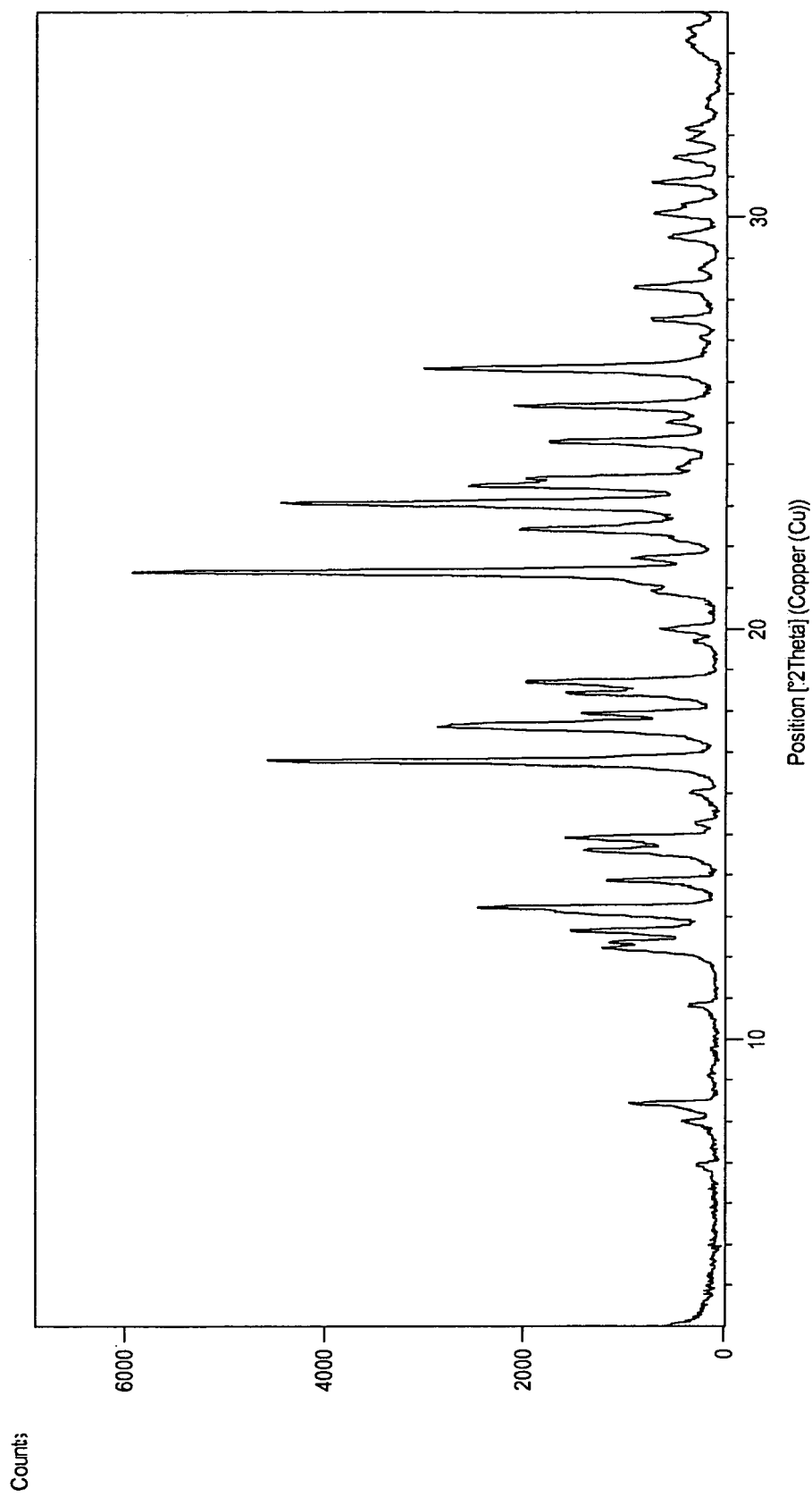
Figure: 1. PXRD of Complex 1 (Pyraclostrobin : 4-hydroxy benzoic acid)

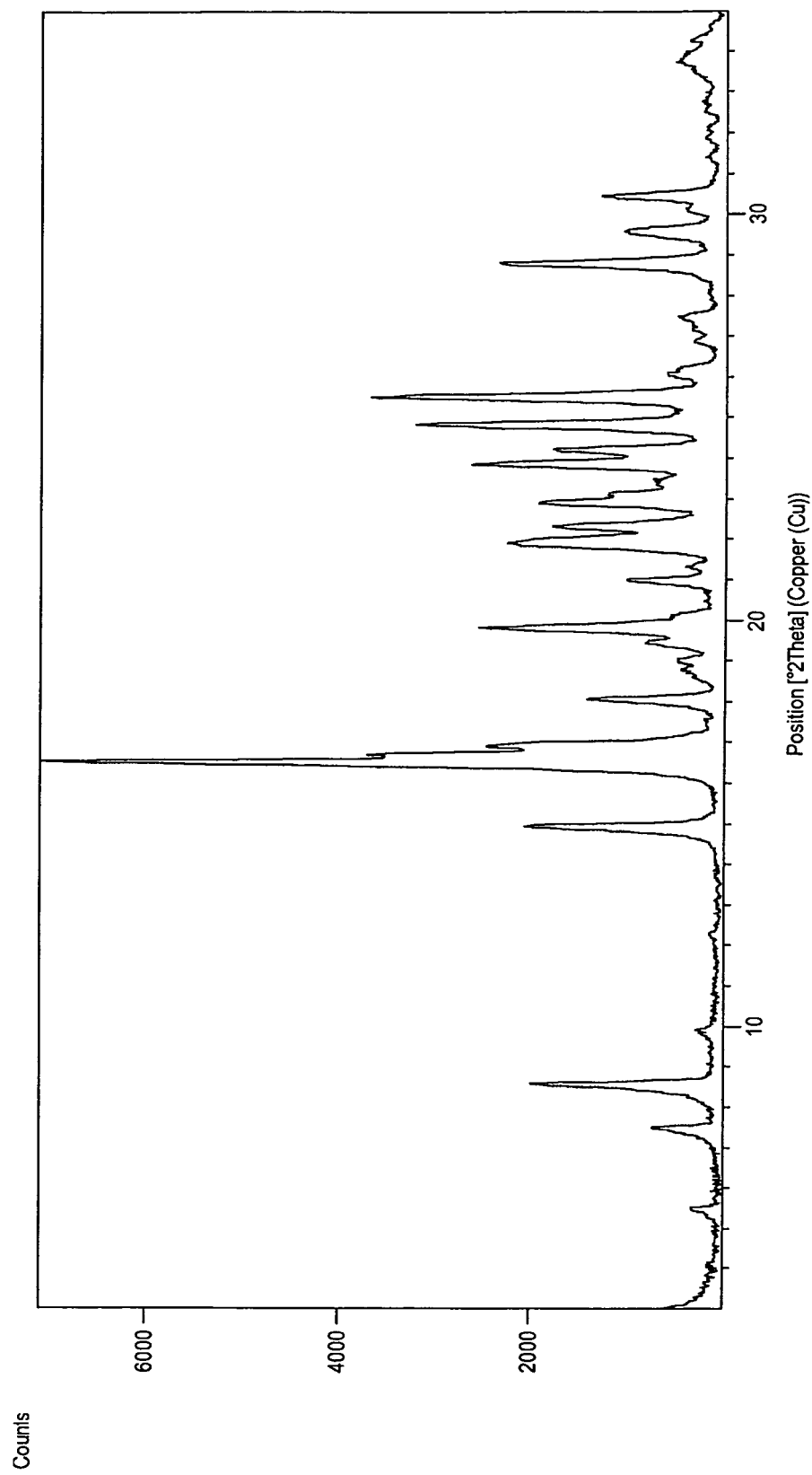
Figure: 2. PXRD of Complex II, (Epoxiconazol : 4-hydroxy benzoic acid)

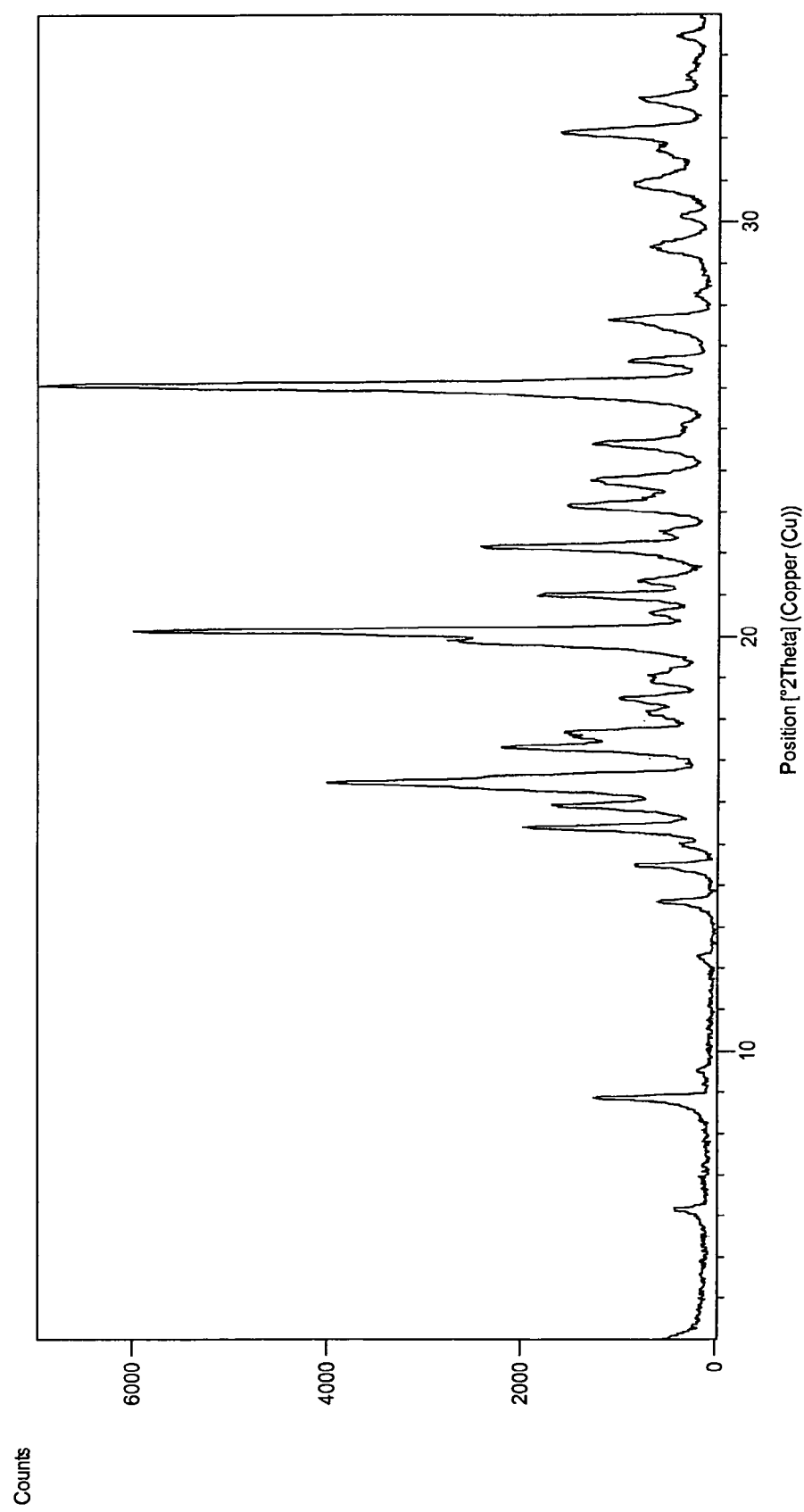
Figure 3: PXRD of Complex III, (tebuconazol : 4-hydroxy benzoic acid)

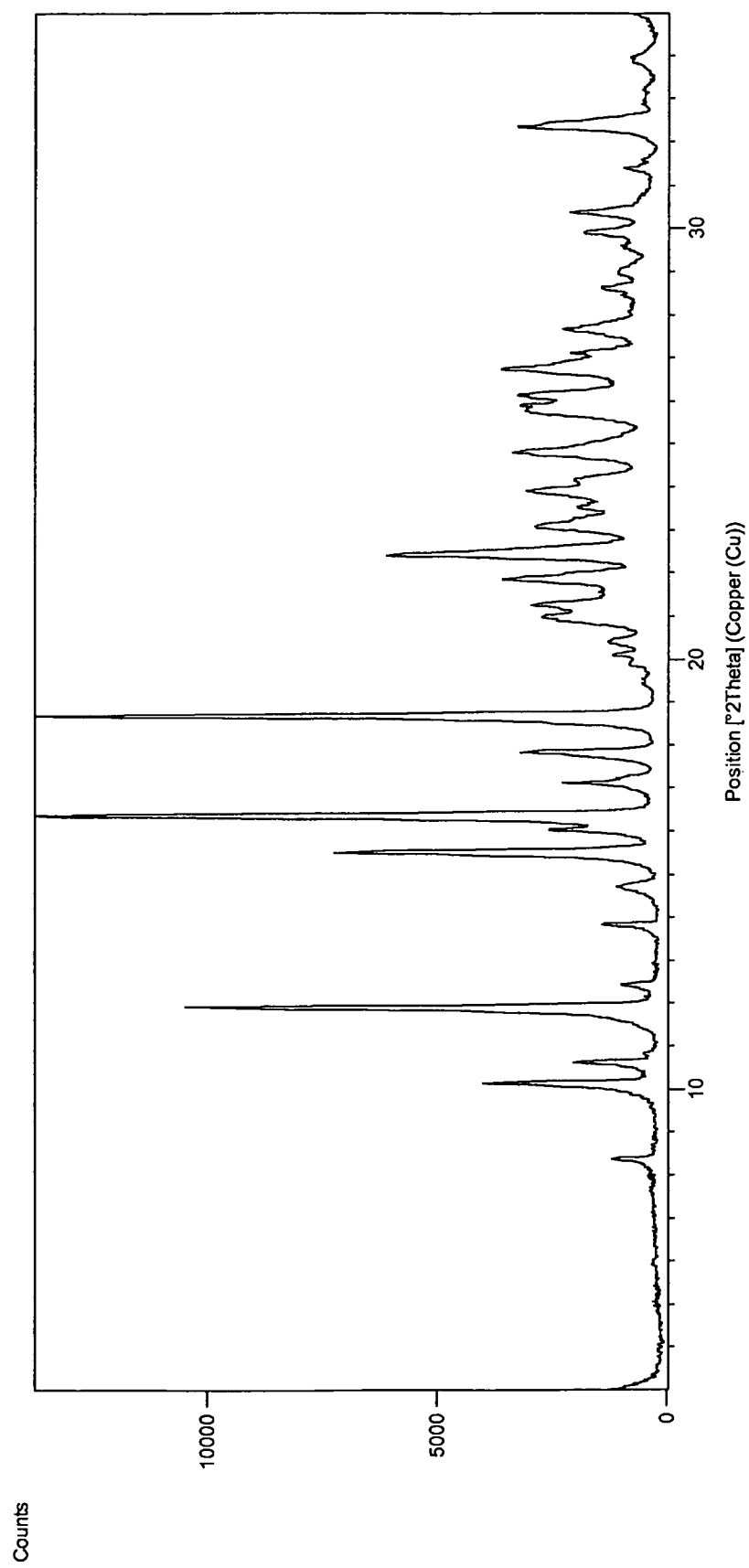
Figure 4. PXRD of Complex IV, (boscalid: 4-hydroxy benzoic acid)

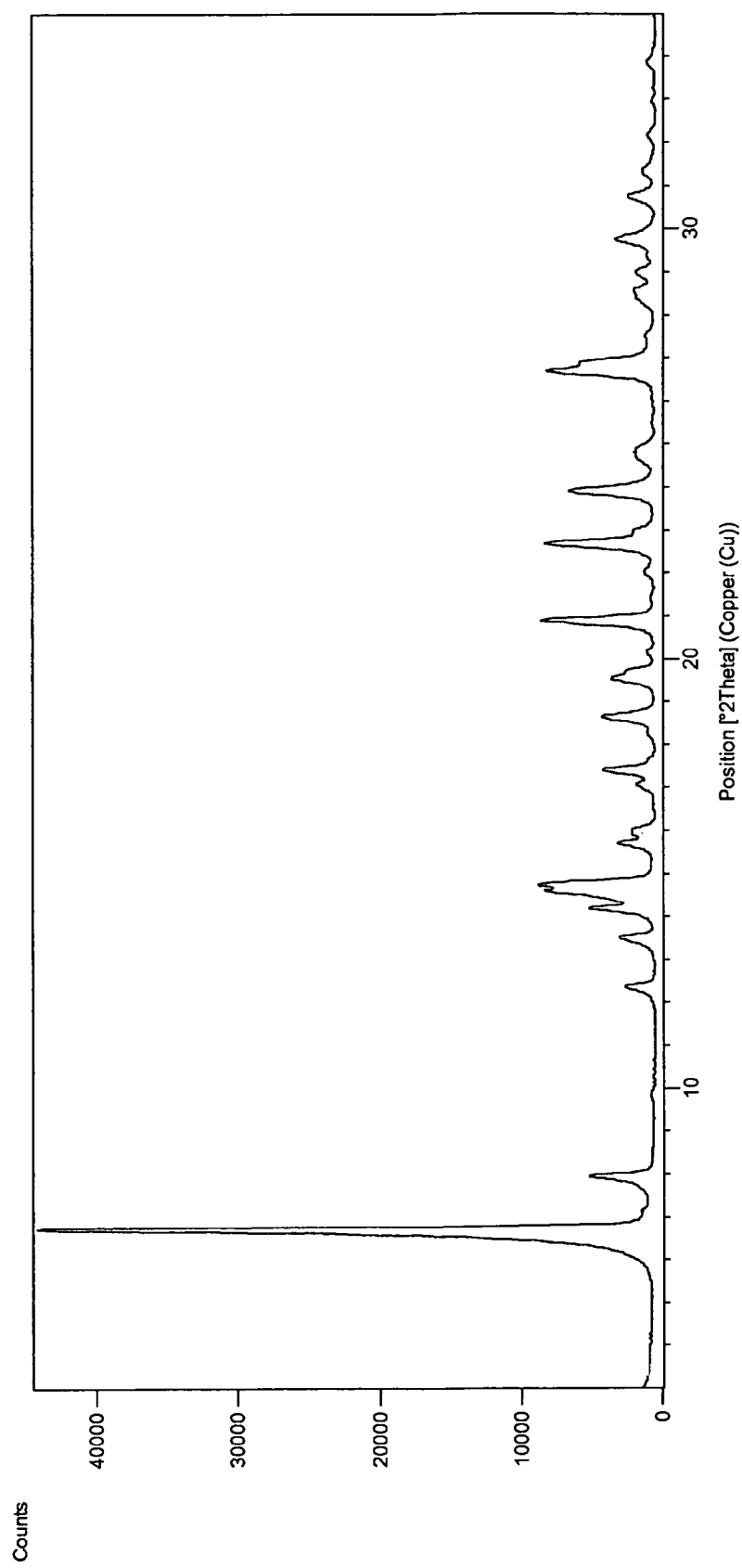
Figure 5. PXRD of Complex V (Imazethapyr : 4-hydroxy benzoic acid)

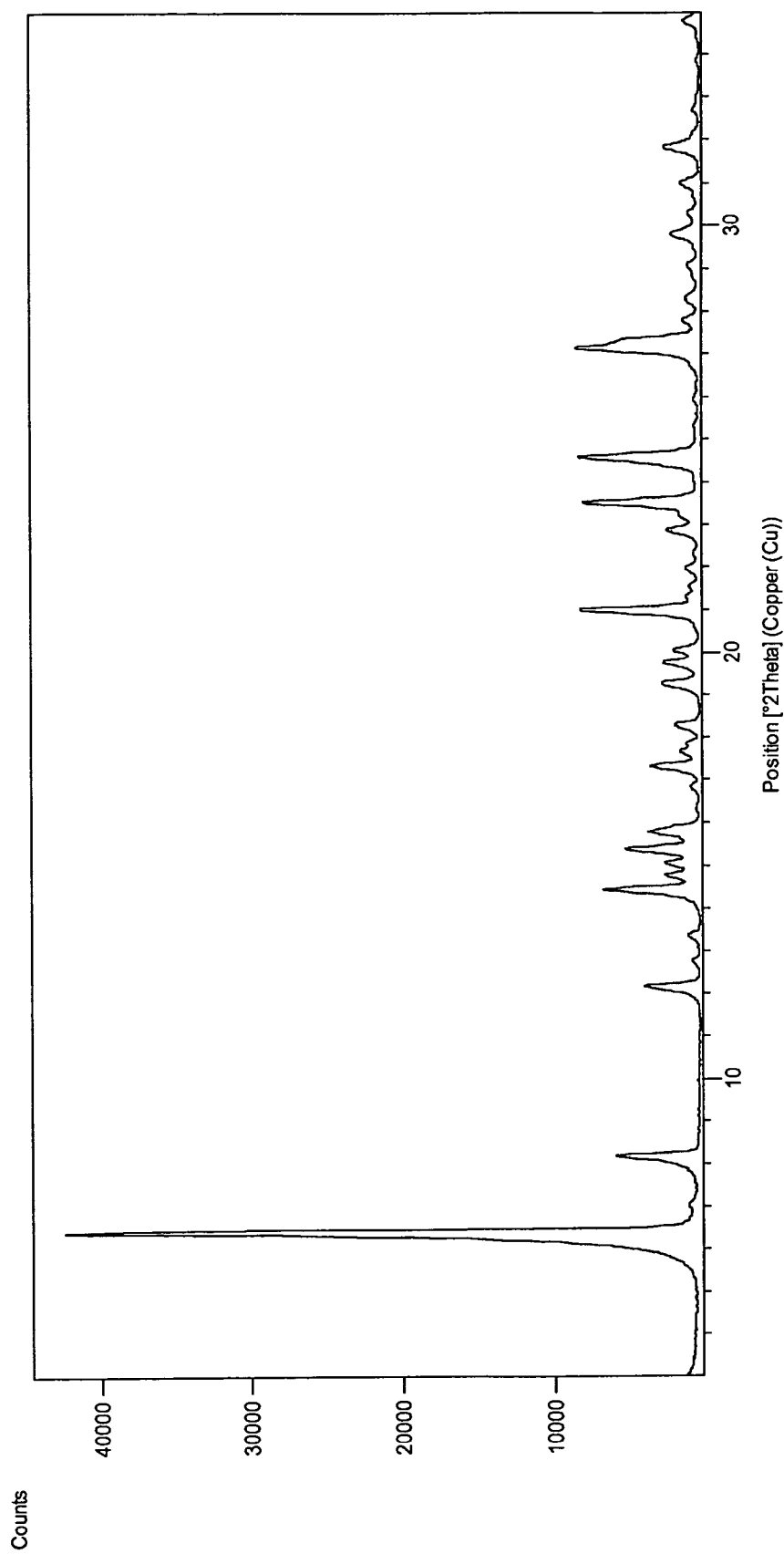
Figure 6. PXRD of Complex VI (Imazamox : 4-hydroxy benzoic acid)

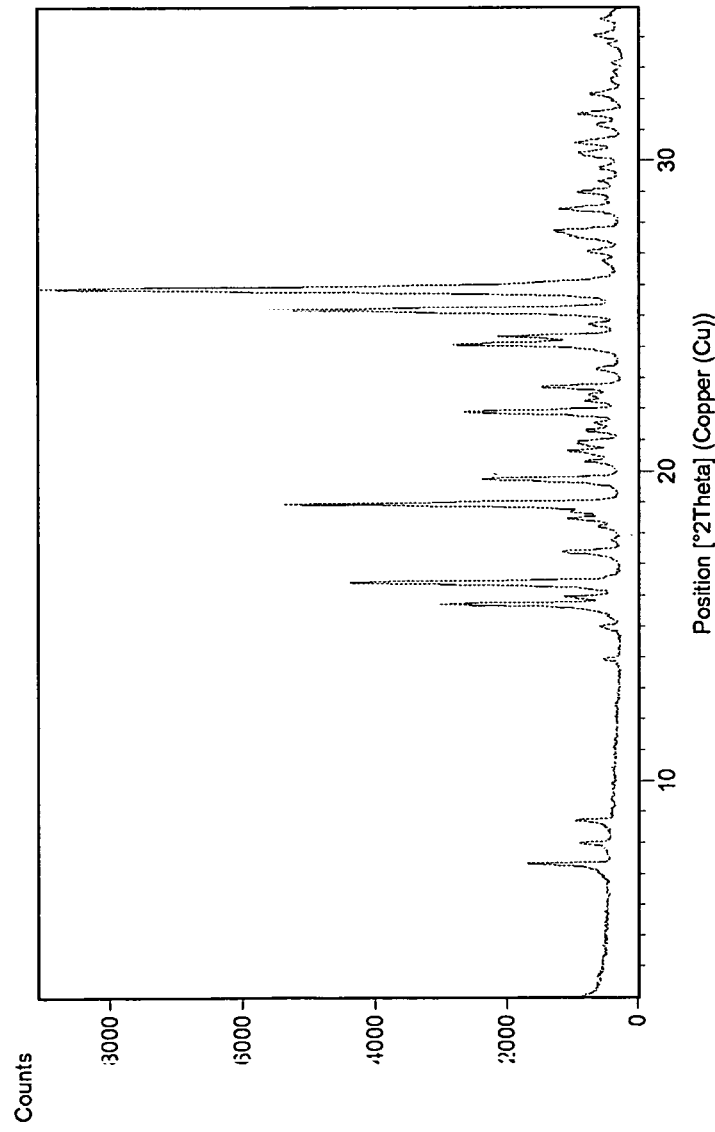
Figure: 7. PXRD of Complex VII, (Acetamiprid : 4-hydroxy benzoic acid)

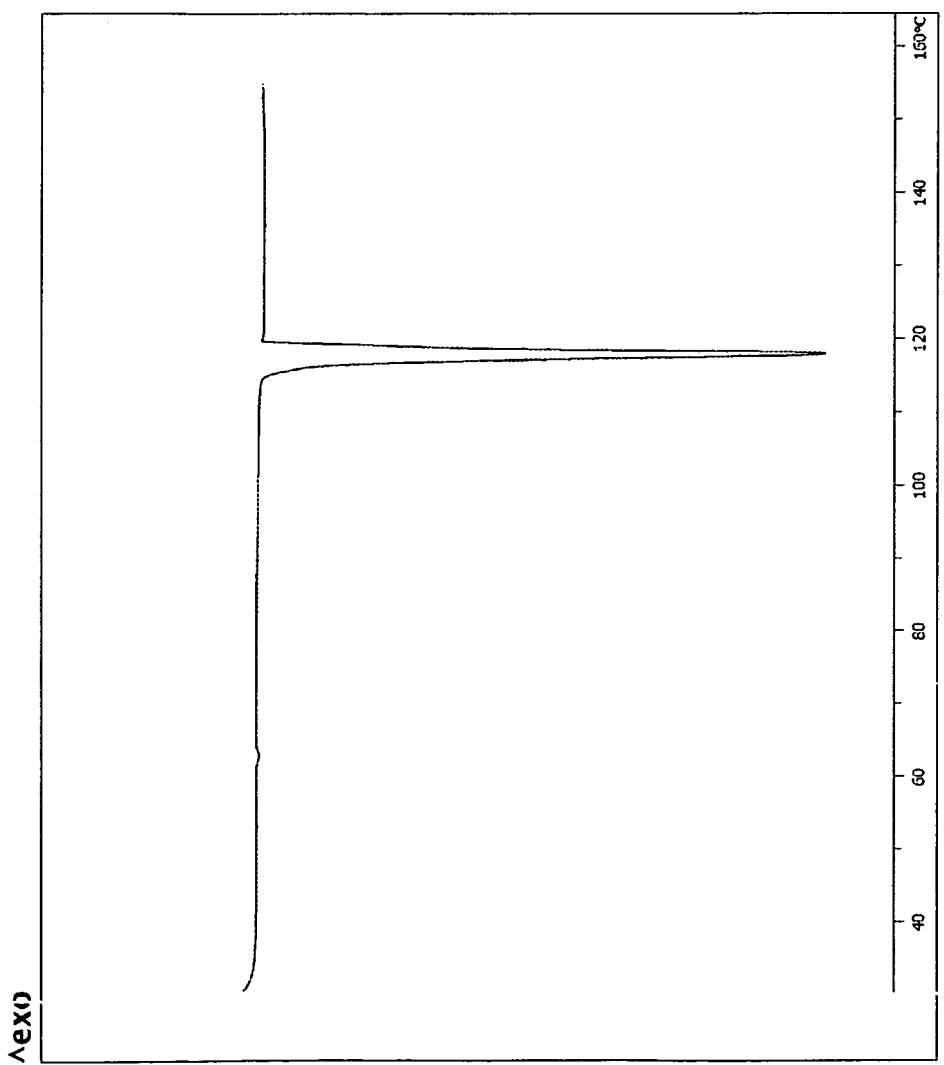
Figure 8. DSC-trace of Complex I

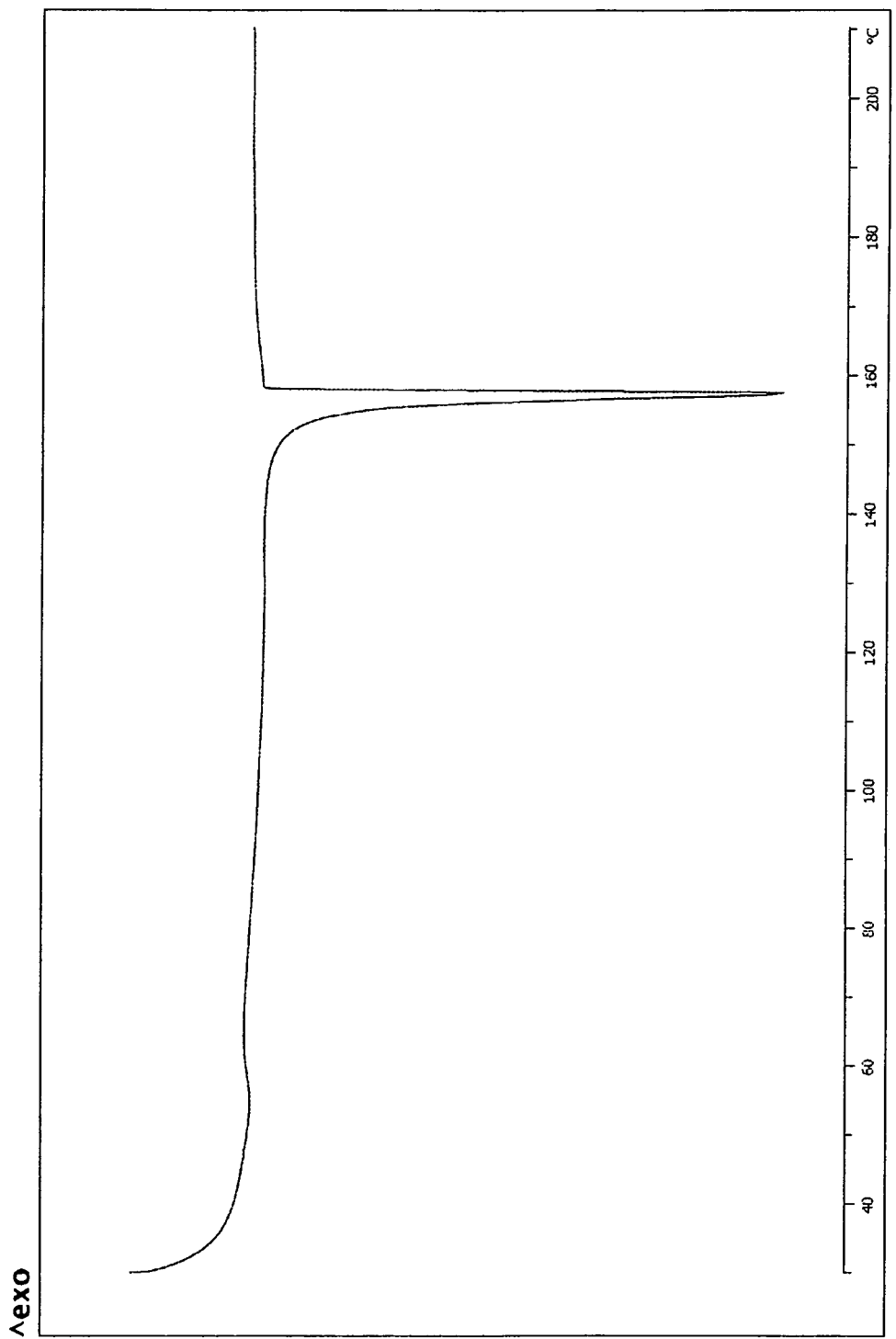
Figure 9. DSC-trace of Complex II

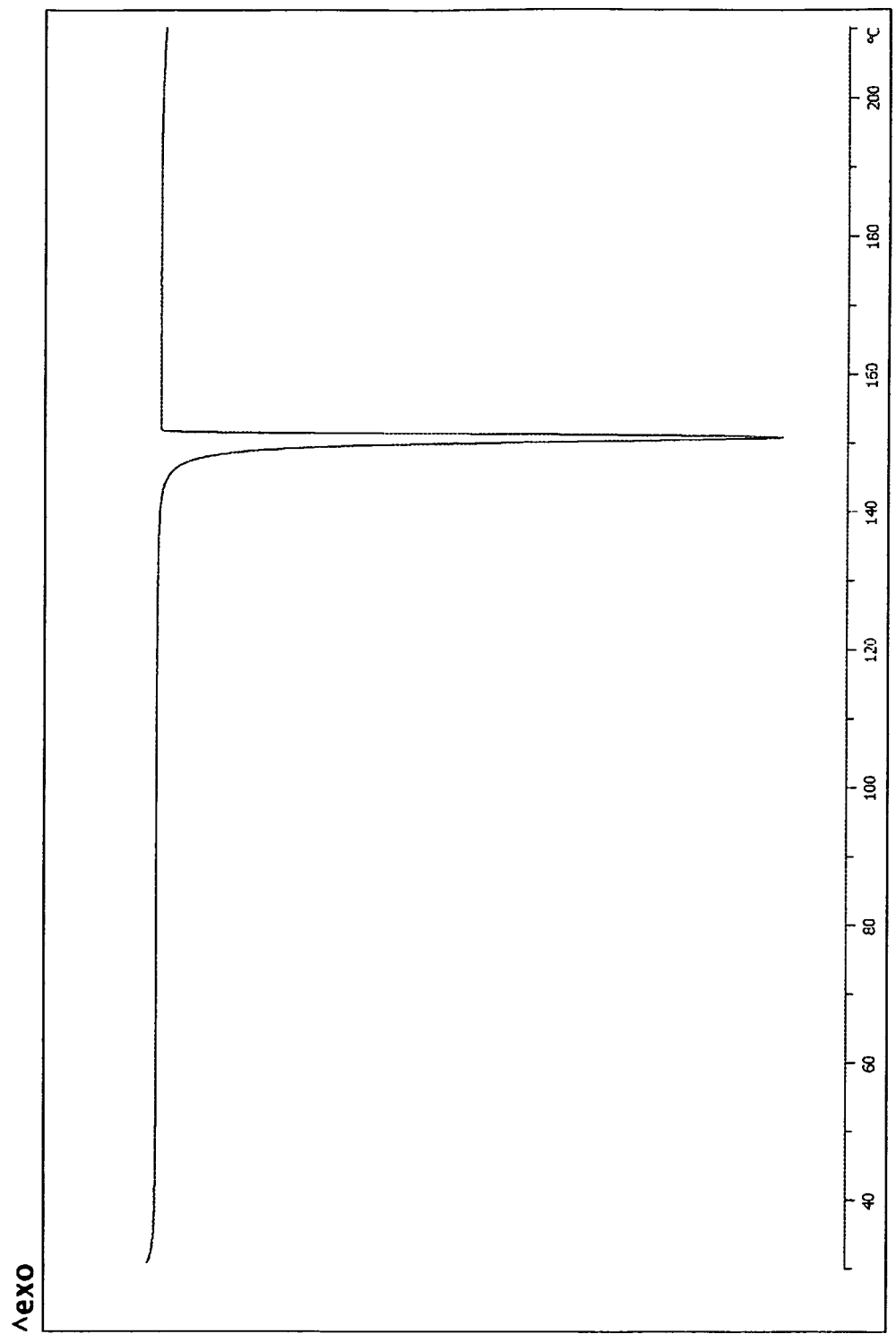
Figure 10. DSC-trace of Complex III

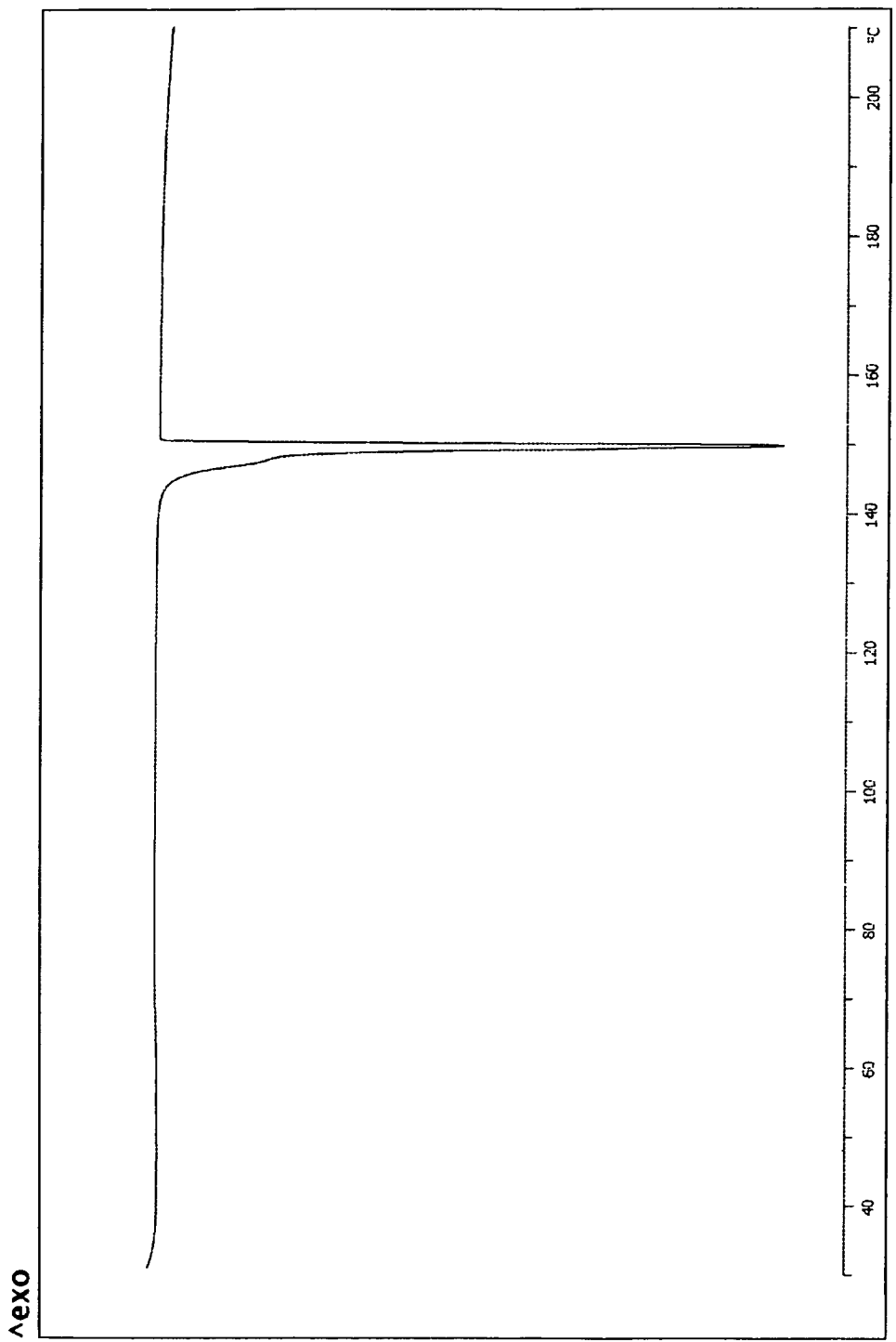
Figure 11. DSC-trace of Complex VI

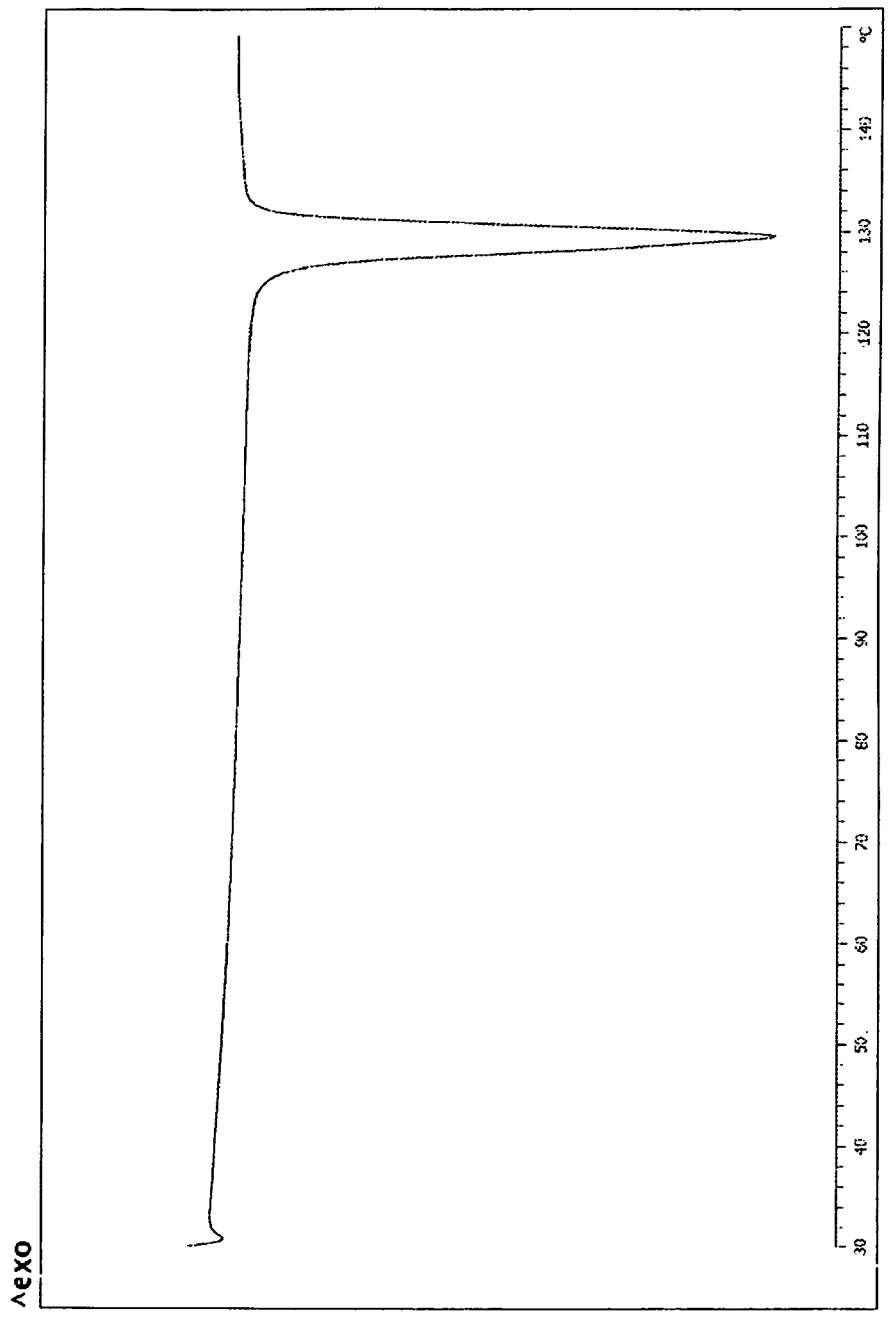
Figure 12. DSC-trace of Complex VII

CRYSTALLINE COMPLEXES OF 4-HYDROXY BENZOIC ACID AND SELECTED PESTICIDES

This application is a National Stage application of International Application No. PCT/EP2010/066401, filed Oct. 28, 2010, the entire contents of which is hereby incorporated herein by reference. This application also claims priority under 35 U.S.C. §119 to European Patent Application No. 09175247.7, filed Nov. 6, 2009, the entire contents of which is hereby incorporated herein by reference.

The present invention relates to crystalline complexes of 4-hydroxy benzoic acid and selected pesticides. It also relates to agriculturally useful compositions of the complexes.

Crystalline complexes of organic compounds, also termed as co-crystals are multicomponent crystals or crystalline materials that consist of at least two different organic compounds which are usually solid at 25° C. or at least a non-volatile oil (vapour pressure less than 1 mbar at 25° C.). In the crystalline complexes (or co-crystals) at least two different organic compounds form a crystalline material having a defined crystal structure, i.e. at least two organic compounds have a defined relative spatial arrangement within the crystal structure.

In the co-crystals, at least two different compounds interact by non-covalent bonding, hydrogen bonds and/or other non-covalent intermolecular forces, including π-stacking, dipole-dipole interactions and van der Waals interactions.

Although the packing in the crystalline lattice cannot be designed or predicted, several supramolecular synthons could successfully be recognized in co-crystals. The term "supramolecular synthon" has to be understood as an entity of usually two compounds that are bonded together via non-covalent interactions, in the most typical case hydrogen bonding. In co-crystals these synthons further pack in the crystalline lattice to form a molecular crystal. Molecular recognition is one condition of the formation of the synthon. However, the co-crystal must also be energetically favourable, i.e. an energy win in the formation of the co-crystal is also required, as molecules typically can pack very efficiently as crystals of pure components thereby hindering the co-crystal formation.

In co-crystals one of the organic compounds may serve as a co-crystal former, i.e. a compound which itself easily forms a crystalline material and which is capable of forming co-crystals with other organic compounds which themselves may not necessarily form a crystalline phase.

Agriculturally active organic compounds (pesticides) such as fungicides, herbicides and insecticides or acaricides are usually marketed as liquid or solid formulations which comprise one or more agriculturally active organic compounds and suitable formulation additives. For several reasons, formulation types are preferred, wherein the agriculturally active organic compound is present in the solid state, examples including solid formulations such as dusts, powders or granules and liquid formulations such as suspension concentrates, i.e. aqueous compositions containing the pesticide as fine particles which are dispersed in the aqueous medium or suspo emulsions, i.e. aqueous compositions containing one pesticide as fine particles which are dispersed in the aqueous medium and a further pesticide solubilized in an organic solvent. Suspension concentrates or suspo-emulsion have the desirable characteristics of a liquid that may be poured or pumped and which can easily be diluted with water to the desired concentration required for application. In contrast to emulsion concentrates the suspension concentrates have the added advantage of not requiring the use of water-immiscible organic solvents. Suspo-emulsions have the advantage of providing the possibility to formulate more than one pesticide in the same concentrate—besides the first active-present in the form of fine particles—the second active can be present solubilized in an organic liquid.

Solid formulations such as granules, powders or any other solid concentrates have the advantage that the pesticide can be formulated at a higher concentration, which provides the advantages of lower production and packaging costs.

For purposes of such solid state formulations the agriculturally active organic compounds should be crystalline materials having a sufficiently high melting point.

Unfortunately, a large number of these organic compounds are amorphous materials resulting in processing difficulties, formulation instabilities and application unreliability due to caking and settling of the fine particles.

A further problem associated with liquid formulations comprising solid pesticides results from the tendency of crystalline material to form large crystals upon aging ("Oswald ripening") resulting in an increased settling of solid pesticide particles and thus in an instability, difficulty in processing and unreliability of usage. Herein, also the morphology of a crystal modification of the pesticide may influence the behaviour of the pesticide in formulation and may even result in different end use properties. For example, a different shape of the pesticide co-crystals vs the pure pesticide crystal may influence the aging process. These problems become most serious when storing respective granules, powders, or other solid concentrates or the suspension concentrates or suspo-emulsions at elevated temperatures above 35° C. and especially above 40° C.

Many pesticides have unsatisfactory low melting points. However, a low melting point does not only complicate the current formulation processes for suspension concentrates and suspo-emulsions or granules, especially in case of the pesticide pyraclostrobin, but might also negatively affect the final formulation stability.

Increasing the melting point provides a solution to this problem.

Besides the issue of melting point increase, there are further tasks the formulation chemist is faced with.

To develop a stable pesticidal formulation, which also exhibits satisfactory pesticidal action is a challenge for the skilled artisan. A central parameter in formulation technology is the control of physico-chemical properties of the pesticide, both in the formulation per se and the application form of the formulation, e.g. in tank mix, wherein the respective formulation is diluted with water. One the hand, the high efficacy of the pesticide, which is required for control of the respective target organism or plant, may have—if not controlled via formulation technology—negative side effects such as toxicity to not-target organisms or agrochemical useful plants. Further unwanted physicochemical properties of pesticides are decay due to processes like breakdown, evaporation and leaching. Thus, object is controlling the physico-chemical the parameters in a way that the pesticide is sufficiently available in a stable formulation concentrate simultaneously avoiding unwanted side effects such as phytotoxicity or toxicity against useful target organisms.

Unfortunately, the techniques available for the skilled artisan to alter the physicochemical properties of a pesticide are very limited.

For example, the reduction of availability of the pesticide, which has in high concentration also unwanted sides as described above can be achieved via encapsulation technologies. These technologies, however, have been proven to be very hard to turn into commercial products either via technical means or via the resulting price of such technology (e.g. as in the case of complexation with cyclodextrins).

It is even more difficult to increase or decrease the availability of a pesticide via formulation technology. Decreased availability of the pesticide could have a desired property, because this may prevent leaching of residual pesticide into the ground water.

Formation of crystalline complexes has been discussed in the past few years as a further potential tool to trigger the availability and stability of the pesticide in formulations, to increase or reduce the availability of a pesticide by amending its physico-chemical properties (such as altered water solubility, melting point, vapour pressure via complexation of the pesticide with a suitable co-former.

However, in most cases, this option is mostly theoretical as suitable crystalline complexes of many pesticides are not known in the art, they are very hard to find for currently used pesticides and the physico-chemical properties of the complexes are not predictable.

Furthermore, for all pesticides, an increased pesticidal action (e.g. fungicidal or herbicidal action) if compared to the solo pesticide is highly desirable as this may lead to a reduction of dose rates.

Furthermore, for all pesticides, a reduced phytotoxicity, which may result in a positive impact on the germination rate in the area of seed treatment, such as an increase of the germination rate of at least 3%, more preferably at least 5% is a highly desired property for the farmer.

Thus, there is a constant need in the art to find novel crystalline complexes of pesticides which have modified physicochemical properties, if compared to the solid state modifications of the pure pesticides.

Crystalline forms of pyraclostrobin and boscalid are known. It is furthermore known to use these crystalline forms in suspension concentrates (WO 06/136357 and WO 04/072039). However, also in these cases, amended physico-chemical properties are highly appreciated as they provide the skilled formulation chemist new tools for developing even better formulations as those currently used in the market.

The object of the present invention was therefore to provide novel crystalline complexes of commercially used pesticides, which show
   a) reduced availability of the pesticide by decreasing its water solubility; and/or,
   b) increased availability of the pesticide; and/or
   c) an increased melting point and/or
   d) enhanced stability in formulations; and/or
   e) change the morphology of the crystals; and/or
   f) a reduced vapour pressure and/or
   g) enhanced pesticidal action and/or
   h) increased germination rate.

This object has been solved by the provision of the novel crystalline complexes comprising
   (I) 4-hydroxybenzoic acid and
   (II) one pesticide selected from pyraclostrobin, epoxiconazole, tebuconazole, imazethapyr, imazamox, acetamiprid and boscalid;

wherein each complex shows at least one of the afore-mentioned properties a), b), c), d), e), f) or g), preferably at least one of the afore-mentioned properties a) c), d), e), h), in particular at least one one of the afore-mentioned properties a), c) and h).

Further details about the technical advantages of each complex are set forth below. 4-Hydroxy benzoic acid is known to have one anyhydrous crystal form and one hydrate (reported in Acta Crystallogr., Sect. C: Cryst. Struct. Commun. 1992, 48, 1960 and Acta Crystallogr., Sect. B: Struct. Crystallogr. Cryst. Chem., 1979, 35, 2177, respectively). Also some solvates and co-crystals of 4-hydroxy benzoic acid have been reported with both neutral and ionic compounds (K. Harata (1977) Bull. Chem. Soc. Jpn., 50, 1416 for a-Cyclodextrin p-hydroxybenzoic acid trihydrate; K. Balasubramani et al (2006), Acta Crystallogr., Sect. E: Struct. Rep. Online, 62, o2907 for 2-amino-4,6-dimethylpyrimidine 4-hydroxybenzoic acid; K. Sawada et al (1998) Bull. Chem. Soc. Jpn., 71, 2109 for tris(Hexadecyl-trimethylammonium)tribromide p-hydroxybenzoic acid monohydrate; K. Sawada et al (1998) Bull. Chem. Soc. Jpn., 71, 2109 for decyl (trimethyl) ammonium bromide p-hydroxybenzoic acid monohydrate; R. E. Marsh, A. L. Spek (2001), Acta Crystallogr., Sect. B: Struct. Sci., 57,800 for decyl (trimetyhl) ammonium bromide p-hydroxybenzoic acid monohydrate; P. Vishweshwar, et al. (2005) Chem. Commun., 4601 for (2-oxo-1-pyrrolodinyl) acetamide p-hydroxybenzoic acid; S. L. Childs, K. I. Hardcastle (2007) Cryst. Growth Des., 7, 1291 for 4-Hydroxy-2-methyl-N-(2-pyridyl)-2H-1,2-benzothiazine-3-carboxamide-1,1-dioxide 4-hydroxybenzoic acid clathrate; K. Gosh et al. (2005), J. Mol. Struct., 434, 201, for hexamethylenetetramine 4-hydroxybenzoic acid; Jian-Rong Su, Duan-Jun Xu (2005), Acta Crystallogr., Sect. E: Struct. Rep. Online, 61, m1738; cis-Aqua-chloro-bis(1,10-phenanthroline)nickel(ii) chloride 4-hydroxybenzoic acid dihydrate; Li-Li Kong, Shan Gao, Li-Hua Huo, S. W. Ng. (2007), Acta Crystallogr., Sect. E: Struct. Rep. Online, 63, m2938 for catena-((u3-3-(4-Carboxylatophenoxy)prpionato-k5O,O":O":O",O"')-(2,2'-bipyridine-k2N,N')cadmium(ii) 4-hydroxybenzoic acid solvate hemihydrate); E. A. Heath, P. Singh, Y. Ebisuzaki (1992), Acta Crystallogr., Sect. C: Cryst. Struct. Commun., 48, 1960, "p-Hydroxybenzoic acid"; E. A. Heath, P. Singh, Y. Ebisuzaki (1992) for Acta Crystallogr., Sect. C: Cryst. Struct. Commun., 48, 1960 for Bis(p-hydroxybenzoic acid) acetone solvate; L. Manojlovic (1968), Acta Crystallogr., Sec. B: Struct. Crystallogr. Cryst. Chem., 24, 326 for potassium hydrogen di(p-hydroxybenzoate)monohydrate; S. L. Childs, G. P. Stahly, A. Park (2007) Mol. Pharmaceutics, 4, 323 for Theophylline 4-hydroxybenzoic acid; M. J. Zaworotko, H. H. Hammud, V. Ch. Kravtsov (2007), J. Cryst. Chem., 37, 219, for tris(1,10-phenanthroline-N,N')-iron (ii) Chloride p-hydroxybenzoate bis(p-hydroxybenzoic acid)heptahydrate; S. L. Childs, K. I. Hardcastle (2007) Cryst. Growth Des., 7, 1291 for 4-Oxy-2-methyl-N-(pyridinium-2-yl)-2H-1,2-benzothiazine-3-carboxamide-1,1-dioxide 4-hydroxybenzoic acid clathrate; B. R. Sreekanth, P. Vishweshwar, K. Vyas (2007), Chem. Comm., 2375 for bis(4-Hydroxybenzoic acid) 2,3,5,6-tetramethylpyrazine; B. R. Sreekanth, P. Vishweshwar, K. Vyas (2007), Chem. Comm., 2375 for bis(4-Hydroxybenzoic acid) 2,3,5,6-tetramethylpyrazine; C. B. Aakeroy et al. (2006), New J Chem., 30, 1452-2-Amino-4-methyl-6-(3-pyridyl)pyrimidine 4-hydroxybenzoic acid; K. Fukuyama et al. (1973), Bull. Chem. Soc. Jpn., 46, 804 for p-Hydroxybenzoic acid monohydrate; M. Colapietro et al (1979), Acta Crystallog., Sect. B: Struct. Crystallogr. Cryst. Chem., 35, 2177 for p-Hydroxybenzoic acid monohydrate; Tiane-Jye Hsieh et al (2005) J. Mol. Struct., 741, 193 for p-Hydroxybenzoic acid monohydrate; Z. Dega-Szafran et al. (2006), J. Mol. Struct., 797, 82 for 1,4-bis(Carboxylatomethyl)-1,4-dimethylpiperazinium bis(p-hydroxybenzoic acid); Z. Dega-Szafran et al. (2003) J. Mol. Struct., 649, 257 for N-Methylmorpholine betaine 4-hydroxybenzoic acid; Z. Dega-Szafran et al. (2006), J. Mol. Struct., 785, 160 for (1,4-dimethylpiperazin-1-ium-1-yl)acetate 4-hydroxybenzoic acid; Z. Dega-Szafran et al. (2007), Pol. J. Chem., 81, 931 for p-Hydroxybenzoic acid piperidinium-3-carboxylate; Z. Dega-Szafran (2008), J. Mol. Struct., 875, 346 for N-methylpiperidine betaine p-hydroxybenzoic acid; P. Vishweshwar et al. (2003), CrystEngComm, 5, 164 for 4-Hydroxybenzoic acid isonicotonamide; C. B. Aakeroy et al. (2007), Chem. Sommun., 3936 for 4-(2-Phenylimidazol-1-yl)methylpyridine 4-hydroxybenzoic acid; M. C. Etter et al. (1991) J. Am. Chem. Soc., 113, 2586 for Diacetamide 4-hydroxybenzoic acid clathrate; G. J. Kemperman et al. (2001) Eur. J. Org. Chem., 3641 for Bis(Cephradine)4-hydroxybenzoic acid tetrahydrate; Lin-Heng Wei (2006), Acta Crystallogr., Sect. E: Struct. Rep. Online, 62, o4506 for Pyridine 4 hydroxybenzoic acid; Skinner, Speakman (1951) J. Chem. Soc., 185 for Rubidium hydrogen di-p-hydroxybenzoate monohydrate; K. Balasubramani et al. (2006), Acta Crystallogr., Sect. E: Struct. Rep. Online, 62, o2907 for 2-Amino-4,6-dimethylpyrimidine 4-hydroxybenzoic acid; P. Vishweshwar et al. (2005) Chem. Commun., 4601 for (2-Oxo-1-pyrrolidinyl)acetamide p-hydroxybenzoic acid; S. L. Childs et al. (2007) Cryst. Growth Des., 7, 1291 for 4-Hydroxy-2-methyl-N-(2-pyridyl)-2H-1,2-benzothiazine-3-carboxamide-1,1-dioxide 4-hydroxybenzoic acid clathrate, K. Ghosh et al. (2005), J. Mol. Struct., 737, 201 for Hexamethylenetetramine 4-hydroxybenzoic acid; E. A. Heath, et al. (1992), Acta Crystallogr., Sect. C: Crysta. Struct. Commun., 48, 1960 for p-Hydroxybenzoic acid; S. L. Childs et al. (2007), Mol. Pharmaceutics, 4, 323 for Theophylline 4-hydroxybenzoic acid; S. L. Childs, K. I. Hardcastle (2007), Cryst. GrowthDes., 7, 1291 for 4-Oxy-2-methyl-N-(pyridinium-2-yl)-2H-1,2-benzothiazine-3-carboxamide-1,1-dioxide 4-hydroxybenzoic acid clathrate; B. R. Sreekanth et al. (2007) Chem. Commun., 2375 for Bis(4-Hydroxybenzoic acid) 2,3,5,6-tetramethylpyrazine; B. R. Sreekanth et al. (2007) Chem. Commun., 2375 for Bis(4-Hydroxybenzoic acid) 2,3,5,6-tetramethylpyrazine; C. B. Aakeroy et al. (2006) New J. Chem., 30, 1452 for 2-Amino-4-methyl-6-(3-pyridyl) pyrimidine 4-hydroxybenzoic acid; Z. Dega-Szafran et al. (2006) J. Mol. Struct., 797, 82 for 1,4-bis(Carboxylatomethyl)-1,4-dimethylpiperazinium bis(p-hydroxybenzoic acid); Z. Dega-Szafran et al. (2003) J. Mol. Struct., 649, 257 for M-Methylmorpholine betaine 4-hydroxybenzoic acid; Z. Dega-Szafran et al. (2006) J. Mol. Struct., 785, 160 for (1,4-dimethylpiperazin-1-ium-1-yl)acetate 4-hydroxybenzoic acid; Z. Dega-Szafran et al. (2007) Pol. J. Chem., 81, 931 for p-Hydroxybenzoic acid piperidinium-3-carboxylate; Z. Dega-Szafran et al. (2008) J. Mol. Struct., 875, 346 for N-methylpiperidine betaine p-hydroxybenzoic acid; P. Vishweshwar et al. (2003) CrystEngCommun, 5, 164 for 4-Hydroxybenzoic acid isonicotinamide; C. B. Aakeroy et al. (2007) Chem. Commun., 3936 for 4-(2-Phenylimidazol-1-yl)methylpyridine 4-hydroxybenzoic acid and M. O. Etter, S. M. Reutzel (1991) J. Am. Chem. Soc., 113, 2586 for diacetamide 4-hydroxybenzoic acid clathrate). WO 08/117060 discloses co-crystals of pesticides with co-formers comprising a carboxylic acid group. However, there were no co-crystals of 4-hydroxy benzoic acid with pesticides described, in particular not with the pesticides of the present invention.

Pyraclostrobin, epoxiconazole, tebuconazole, imazethapyr, imazamox, boscalid and acetamiprid as well as their pesticidal action and methods for producing them are generally known. For instance, the commercially available compounds may be found in The Pesticide Manual, 14th Edition, British Crop Protection Council (2006) among other publications.

Co-crystals of any of the afore-mentioned pesticides with 4-hydroxy-benzoic acid have not yet been described.

Thus, the present invention relates to crystalline complexes comprising 4-hydroxybenzoic acid and pyraclostrobin (hereinbelow referred to as "Complex I").

In a further embodiment, the present invention relates to crystalline complexes comprising 4-hydroxybenzoic acid and epoxiconazole (hereinbelow referred to as "Complex II").

In a further embodiment, the present invention relates to crystalline complexes comprising 4-hydroxybenzoic acid and tebuconazole (hereinbelow referred to as "Complex III").

In a further embodiment, the present invention relates to crystalline complexes comprising 4-hydroxybenzoic acid and boscalid (hereinbelow referred to as "Complex IV").

In a further embodiment, the present invention relates to crystalline complexes comprising 4-hydroxybenzoic acid and imazethapyr (hereinbelow referred to as "Complex V").

In a further embodiment, the present invention relates to crystalline complexes comprising 4-hydroxybenzoic acid and imazamox (hereinbelow referred to as "Complex VI").

In a further embodiment, the present invention relates to crystalline complexes comprising 4-hydroxybenzoic acid and acetamprid (hereinbelow referred to as "Complex VII").

In particular, complex I shows a markedly increased melting point, if compared to the melting point of the crystalline pesticide, which facilitates the production of SC and/or SE formulations or granular formulations, if compared to the crystalline pyraclostrobin alone. Complex I also provides an increased germination rate, if compared to the pesticide present in the complex alone.

Complex II shows an increased melting point, if compared to the melting point of the crystalline pesticide, which facilitates the production of SC and/or SE or granular formulations, if compared to the crystalline epoxiconazole alone.

Complex III shows a markedly increased melting point, if compared to the melting point of the crystalline pesticide, which facilitates the production of SC and/or SE formulations, if compared to the crystalline tebuconazole alone Complex V shows a markedly decreased solubility in water, if compared to solubility in water of the crystalline pesticide, which is advantageous for the reasons given above Complex VII shows an increased melting point, if compared to the melting point of the crystalline pesticide, which facilitates the production of SC and/or SE formulations or granular formulations, if compared to the crystalline acetamiprid alone. Complex VII shows also a markedly decreased solubility in water, if compared to solubility in water of the crystalline pesticide, with the increase of the stability of the formulation if compared to the crystalline acetamiprid alone Preferred are the crystalline complexes I, II and VII, more preferred are the complexes I and II, most preferred is complex I Moreover, the formulations of such crystalline complexes show increased stability, in particular in comparison with formulations containing a mixture of 4-hydroxybenzoic acid and the respective pesticide II as individual solid compounds In complex I, the molar ratio of 4-hydroxybenzoic acid and pyraclostrobin is generally in the range from 2:1 to 1:2, preferably from 1.5:1 to 1:1.5, and in particular from 1:1. However, deviations are possible, though they will generally not exceed 20 mol-% and preferably not exceed 10 mol-%.

In complex II, the molar ratio of 4-hydroxybenzoic acid and epoxiconazole is generally in the range from 2:1 to 1:2, preferably from 1.5:1 to 1:1.5, and in particular from 1:1. However, deviations are possible, though they will generally not exceed 20 mol-% and preferably not exceed 10 mol-%.

In complex III, the molar ratio of 4-hydroxybenzoic acid and tebuconazole is generally in the range from 10:1 to 1:10, preferably from 4:1 to 1:4, more preferably from 2:1 to 1:2 (e.g. ratios such as 1:2, 2:1, 1:1).

However, deviations are possible, though they will generally not exceed 20 mol-% and preferably not exceed 10 mol-%.

In complex IV, the molar ratio of 4-hydroxybenzoic acid and boscalid is generally in the range from 10:1 to 1:10, preferably from 4:1 to 1:4, more preferably from 2:1 to 1:2 (e.g. ratios such as 1:2, 2:1, 1:1).

However, deviations are possible, though they will generally not exceed 20 mol-% and preferably not exceed 10 mol-%.

In complex V, the molar ratio of 4-hydroxybenzoic acid and imazethapyr is generally in the range from 10:1 to 1:10, preferably from 4:1 to 1:4, more preferably from 2:1 to 1:2 (e.g. ratios such as 1:2, 2:1, 1:1), in particular in the range from 1.5:1 to 1:1.5, and in particular from 1:1. However, deviations are possible, though they will generally not exceed 20 mol-% and preferably not exceed 10 mol-%.

In complex VI, the molar ratio of 4-hydroxybenzoic acid and imazamox is generally in the range from 10:1 to 1:10, preferably from 4:1 to 1:4, more preferably from 2:1 to 1:2 (e.g. ratios such as 1:2, 2:1, 1:1). However, deviations are possible, though they will generally not exceed 20 mol-% and preferably not exceed 10 mol-%.

In complex VII, the molar ratio of 4-hydroxybenzoic acid and acetamiprid are generally in the range from 10:1 to 1:10, preferably from 4:1 to 1:4, more preferably in the range from 2:1 to 1:2 (e.g. ratios such as 1:2, 2:1, 1:1). However, deviations are possible, though they will generally not exceed 20 mol-% and preferably not exceed 10 mol-%.

The crystalline complexes can be distinguished from simple mixtures of crystalline 4-hydroxybenzoic acid and the respective pesticide by standard analytical means used for the analysis of crystalline material, including X-ray powder diffractometry (PXRD), single crystal X-ray diffractometry (when single crystals of sufficient quality are available) and thermochemical analysis such as thermogravimetry (TGA) and differential scanning calorimetry (DSC) or by spectrometrical methods, such as solid state NMR (for example $^{13}$C CPMAS), FT-IR or Raman. Relative amounts of 4-hydroxybenzoic acid and the respective pesticide Ican be determined e.g. by HPLC or by $^1$H-NMR-spectroscopy.

Further details of each complex are set hereinbelow:

The crystalline complex of 4-hydroxybenzoic acid and pyraclostrobin (complex I) shows an X-ray powder diffractogram at 25° C. (Cu—Kα radiation, 1.54060 Å;) wherein the characteristic reflexes of the pure compounds are missing. In particular, the crystalline complex of 4-hydroxybenzoic acid and pyraclostrobin shows at least 5, preferably at least 7, in particular at least 9 and more preferably all of the following reflexes, given in the following table 1 as 2θ values or as lattice spacings d:

TABLE 1

PXRD of the crystalline complex of 4-hydroxybenzoic acid and pyraclostrobin (25° C., Cu-radiation, 1.5406 Å)

| 2θ values | d [Å] |
|---|---|
| 6.98 ± 0.2° | 12.65 |
| 8.02 ± 0.2° | 11.02 |
| 8.46 ± 0.2° | 10.46 |
| 10.82 ± 0.2° | 8.17 |
| 12.24 ± 0.2° | 7.23 |
| 12.66 ± 0.2° | 6.99 |
| 13.23 ± 0.2° | 6.69 |
| 14.93 ± 0.2° | 5.93 |
| 16.80 ± 0.2° | 5.28 |
| 17.64 ± 0.2° | 5.03 |

TABLE 1-continued

PXRD of the crystalline complex of 4-hydroxybenzoic acid and pyraclostrobin (25° C., Cu-radiation, 1.5406 Å)

| 2θ values | d [Å] |
|---|---|
| 18.74 ± 0.2° | 4.74 |
| 21.40 ± 0.2° | 4.15 |
| 23.09 ± 0.2° | 3.85 |
| 25.42 ± 0.2° | 3.06 |
| 26.33 ± 0.2° | 3.38 |

The crystalline Complex I has typically a melting point in the range from 114 to 120° C., in particular in the range from 114 to 116° C.

The crystalline complex of 4-hydroxybenzoic acid and epoxiconazol (complex II) shows an X-ray powder diffractogram at 25° C. (Cu—Kα radiation, 1.54060 Å;) wherein the characteristic reflexes of the pure compounds are missing. In particular, the crystalline complex of 4-hydroxybenzoic acid and epoxiconazol shows at least 5, preferably at least 7, in particular at least 9 and more preferably all of the following reflexes, given in the following table 1 as 2θ values or as lattice spacings d:

TABLE 3

PXRD of the crystalline complex of 4-hydroxybenzoic acid and epoxiconazol (25° C., Cu-radiation, 1.5406 Å)

| 2θ values | d [Å] |
|---|---|
| 5.49 ± 0.2° | 16.08 |
| 7.50 ± 0.2° | 11.79 |
| 8.59 ± 0.2° | 10.30 |
| 9.86 ± 0.2° | 8.97 |
| 14.96 ± 0.2° | 5.92 |
| 16.51 ± 0.2° | 5.37 |
| 16.99 ± 0.2° | 5.22 |
| 19.82 ± 0.2° | 4.48 |
| 21.91 ± 0.2° | 4.06 |
| 25.52 ± 0.2° | 3.49 |
| 28.80 ± 0.2° | 3.10 |
| 30.47 ± 0.2° | 2.93 |

The single crystal structure of Complex II was determined at −170° C. The crystal structure of the crystalline complex of 4-hydroxybenzoic acid and epoxiconazol has a monoclinic crystal system and the space group is P 2$_1$/c. The crystallographical parameters are reported in table 4.

The structure analysis reveals that the crystalline complex is a 1:1 mixture of 4-hydroxybenzoic acid and epoxiconazol with the asymmetric unit containing one molecule of 4-hydroxybenzoic acid and epoxiconazol, each. The spatial arrangement of the 4-hydroxybenzoic and epoxiconazol molecules in the crystal seems to be mainly driven H-bonding in between two 4-hydroxy benzoic acid molecules and also H-bonding in between 4-hydroxy benzoic acid and epoxiconazol molecules.

The crystalline complex II has typically a melting point in the range from 149 to 155° C., in particular in the range from 149 to 153° C.

The crystalline complex of 4-hydroxybenzoic acid and tebuconazol (complex III) shows an X-ray powder diffractogram at 25° C. (Cu—Kα radiation, 1.54060 Å;) wherein the characteristic reflexes of the pure compounds are missing. In particular, the crystalline complex of 4-hydroxybenzoic acid and tebuconazol shows at least 4, preferably at least 6, in particular at least 8 and more preferably all of the following reflexes, given in the following table 1 as 2θ values or as lattice spacings d:

TABLE 5

PXRD of the crystalline complex of 4-hydroxybenzoic acid and tebuconazol (25° C., Cu-radiation, 1.5406 Å)

| 2θ values | d [Å] |
|---|---|
| 6.19 ± 0.2° | 14.29 |
| 8.88 ± 0.2° | 9.96 |
| 14.51 ± 0.2° | 6.11 |
| 15.41 ± 0.2° | 5.75 |
| 16.39 ± 0.2° | 5.41 |
| 16.48 ± 0.2° | 5.38 |
| 20.15 ± 0.2° | 4.41 |
| 22.19 ± 0.2° | 4.01 |
| 26.08 ± 0.2° | 3.42 |
| 27.64 ± 0.2° | 3.23 |
| 32.20 ± 0.2° | 2.78 |

The crystalline Complex III has typically a melting point in the range from 148 to 153° C., in particular in the range from 148 to 149° C.

The crystalline complex of 4-hydroxybenzoic acid and boscalid (complex IV) shows an X-ray powder diffractogram at 25° C. (Cu—Kα radiation, 1.54060 Å;) wherein the characteristic reflexes of the pure compounds are missing. In particular, the crystalline complex of 4-hydroxybenzoic acid and boscalid shows at least 5, preferably at least 7, in particular at least 9 and more preferably all of the following reflexes, given in the following table 1 as 2θ values or as lattice spacings d:

TABLE 6

PXRD of the crystalline complex of 4-hydroxybenzoic acid and boscalid (25° C., Cu-radiation, 1.5406 Å)

| 2θ values | d [Å] |
|---|---|
| 8.38 ± 0.2° | 10.55 |
| 10.15 ± 0.2° | 8.72 |
| 10.65 ± 0.2° | 8.31 |
| 11.92 ± 0.2° | 7.41 |
| 15.53 ± 0.2° | 5.70 |
| 16.39 ± 0.2° | 5.41 |
| 17.84 ± 0.2° | 4.97 |
| 18.70 ± 0.2° | 4.75 |
| 21.85 ± 0.2° | 4.07 |
| 22.41 ± 0.2° | 3.97 |
| 26.75 ± 0.2° | 3.33 |
| 32.34 ± 0.2° | 2.77 |

The crystalline complex IV has typically a melting point in the range from 145 to 155° C., in particular in the range from 148 to 150° C.

The melting point of the crystalline complex is thus ~10° C. higher than the melting point of boscalid.

The crystalline complex of 4-hydroxybenzoic acid and imazethapyr (complex V) shows an X-ray powder diffractogram at 25° C. (Cu—Kα radiation, 1.54060 Å;) wherein the characteristic reflexes of the pure compounds are missing. In particular, the crystalline complex of 4-hydroxybenzoic acid and imazethapyr shows at least 4, preferably at least 6, in particular at least 8 and more preferably all of the following reflexes, given in the following table 1 as 2θ values or as lattice spacings d:

TABLE 7

PXRD of the crystalline complex of 4-hydroxybenzoic acid and imazethapyr (25° C., Cu-radiation, 1.5406 Å)

| 2θ values | d [Å] |
|---|---|
| 6.76 ± 0.2° | 13.08 |
| 7.98 ± 0.2° | 11.07 |
| 12.39 ± 0.2° | 7.14 |
| 14.82 ± 0.2° | 5.98 |
| 15.73 ± 0.2° | 5.63 |
| 16.06 ± 0.2° | 5.51 |
| 20.92 ± 0.2° | 4.24 |
| 22.70 ± 0.2° | 3.92 |
| 26.71 ± 0.2° | 3.34 |
| 30.74 ± 0.2° | 2.91 |

The crystalline Complex V has typically a melting point in the range from 152 to 161° C., in particular in the range from 153 to 159° C.

The crystalline complex of 4-hydroxybenzoic acid and imazamox (complex VI) shows an X-ray powder diffractogram at 25° C. (Cu—Kα radiation, 1.54060 Å;) wherein the characteristic reflexes of the pure compounds are missing. In particular, the crystalline complex of 4-hydroxybenzoic acid and imazamox shows at least 4, preferably at least 6, in particular at least 8 and more preferably all of the following reflexes, given in the following table 1 as 2θ values or as lattice spacings d.

TABLE 9

PXRD of the crystalline complex of 4-hydroxybenzoic acid and imazamox (25° C., Cu-radiation, 1.5406 Å)

| 2θ values | d [Å] |
|---|---|
| 6.44 ± 0.2° | 13.73 |
| 8.21 ± 0.2° | 10.76 |
| 12.20 ± 0.2° | 7.25 |
| 14.48 ± 0.2° | 6.12 |
| 15.39 ± 0.2° | 5.75 |
| 15.84 ± 0.2° | 5.59 |
| 17.33 ± 0.2° | 5.12 |
| 21.02 ± 0.2° | 4.22 |
| 23.54 ± 0.2° | 3.78 |
| 24.61 ± 0.2° | 3.61 |
| 27.16 ± 0.2° | 3.28 |
| 31.85 ± 0.2° | 2.74 |

The crystalline complex VI has typically a melting point in the range from 145 to 155° C., in particular in the range from 148 to 150° C.

The crystalline complex of 4-hydroxybenzoic acid and acetamiprid (complex VII) shows an X-ray powder diffractogram at 25° C. (Cu—Kα radiation, 1.54060 Å;) wherein the characteristic reflexes of the pure compounds are missing. In particular, the crystalline complex of 4-hydroxybenzoic acid and acetamiprid shows at least 4, preferably at least 6, in particular at least 8 and more preferably all of the following reflexes, given in the following table 11 as 2θ values or as lattice spacings d:

TABLE 11

PXRD of the crystalline complex of 4-hydroxybenzoic acid and acetamirid (25° C., Cu-radiation, 1.5406 Å)

| 2θ values | d [Å] |
|---|---|
| 7.33 ± 0.2° | 12.06 |
| 8.00 ± 0.2° | 11.05 |

TABLE 11-continued

PXRD of the crystalline complex of 4-hydroxybenzoic acid and acetamirid (25° C., Cu-radiation, 1.5406 Å)

| 2θ values | d [Å] |
|---|---|
| 8.73 ± 0.2° | 10.13 |
| 15.74 ± 0.2° | 5.63 |
| 16.44 ± 0.2° | 5.39 |
| 18.96 ± 0.2° | 4.68 |
| 21.93 ± 0.2° | 4.05 |
| 24.09 ± 0.2° | 3.69 |
| 25.21 ± 0.2° | 3.53 |
| 25.89 ± 0.2° | 3.44 |

The present invention also comprises a process for preparing the co-crystal or complex of the present invention as defined in any of the preceding claims, which comprises combining 4-hydroxy benzoic acid and the pesticide (II) in suitable solvent.

In one embodiment of the present invention, hereinafter referred to as "Solution process" 4-hydroxy benzoic acid and the pesticide are completely dissolved in a suitable solvent, wherein in a second step co-crystallization is induced by cooling ("Cooling process") or evaporation ("Evaporation process") or precipitation ("Precipitation process").

In a further embodiment of the present invention, hereinafter referred to as "Shear process" 4-hydroxy benzoic acid and the pesticide II are combined together by applying shear forces to the combined pesticide II and 4-hydroxy benzoic acid.

In a further embodiment of the present invention, hereinafter referred to as "Slurry process" 4-hydroxy benzoic acid and the pesticide II are suspending 4-hydroxybenzoic acid and pesticide II in an suitable solvent.

In all of the preparation process variants, the respective liquid media used in the processes may also include additives which are usually present in agrochemical formulations, if appropriate. Suitable additives are described hereinafter and include surfactants, in particular anionic or non-ionic emulsifiers, wetting agents and dispersants usually employed in crop protection compositions, furthermore antifoam agents, antifreeze agents, agents for adjusting the pH, stabilizers, anticaking agents, dyes and biocides (preservatives). The amount of the individual components will vary depending on the final formulation type. Examples of these auxiliaries are set forth hereinblow.

a) As described above, the "Solution process" is to be understood as a process where the pesticide II and 4-hydroxy benzoic acid is fully dissolved in a solvent system at a specific temperature and where the crystallization of the co-crystal is induced either by a cooling, evaporation or precipitation processes.

Herein, saturated solutions of the pesticide II and 4-hydroxybenzoic acid can be prepared separately at an elevated temperature (for example in the case of pyraclostrobin in the range of 50 to 120° C., in case of the other pesticides II, these temperatures could be higher: from 50 to 150° C. in the case of epoxiconazole, tebuconazole, boscalid, imazethapyr and imazamox. Afterwards, both solutions can be combined at the same temperature and cooled down to 0 to 20° C., preferably to 3 to 8° C. (e.g. 5° C.). The crystalline complexes present resulting suspension can be separated from the resulting suspension by conventional techniques (e.g. filtration). This process is hereinbelow after referred to as "Cooling Process". The pesticide II and 4-hydroxy benzoic acid can be also brought to solution by dissolving them at elevated temperature simultaneously in the same vessel and then applying the above described cooling process. Herein, the absolute amounts and ratio of pesticide II and 4-hydroxy benzoic acid need to be chosen case by case depending of the phase diagram of the system in the corresponding solvent system considering for example the solubility of the compounds, the ratio of the co-crystal and possibility for polymorphism and solvate formation. Preferred solvents are those, where 4-hydroxybenzoic acid and pesticide II have a comparable solubility. Comparable solubility means that the solubilities of the individual compounds in the solvent or solvent system differ by preferably a factor of not more than 20, more preferably a factor of 10 and in particular by a factor of not more than 5.

In an evaporation crystallization, from now on called as the "Evaporation process" the solution of pesticide II and 4-Hydroxy benzoic acid is prepared in accordance with the conditions set forth for the Cooling process crystallization with the following differences:
1. The Evaporation process lower temperatures can be used if compared to the Cooling process.
2. In the solvents of the Evaporation process 4-hydroxybenzoic acid and pesticide II should have a similar solubility. Similar solubility means that the solubilities of the individual compounds in the solvent or solvent system differ by more than 10%, in particular by a factor of not more than 5%.

After dissolving the two components in the selected solvent, the solvent is removed by using commonly used evaporation techniques (e.g. evaporation by heating or reduced pressure).

In a precipitation crystallization, from here on called as "Precipitation process" the pesticide II is brought into solution with 4-hydroxy benzoic acid as described above for Cooling process and Evaporation process. The crystallization is induced by lowering the solubility of the solvent system by addition of a solvent, in which the solubility of pesticide II and solubility of 4-hydroxy benzoic is preferably lower than 10 g/l and in particular lower than 2 g/l at room temperature (hereinbelow referred to as "anti-solvent"). A convenient suitable anti-solvent is water. The amount of the anti-solvent and method of addition (step wise or over a longer period) depend of the pesticide II and the used solvent system. The solvents suitable for the precipitation process need to be miscible at least with the anti-solvent.

Principally, the pesticide II needs to be sufficiently soluble in the solvent, which means a solubility of more than 10 g, more preferably in between 100 and 500 g/l of pesticide II/l at 20° C.

Suitable solvents for the Cooling Process and the Evaporation Process are organic solvents having a water miscibility of at least 10% at room temperature ("polar organic solvents") or mixtures of water with a polar organic solvents or organic solvents having a water miscibility of below 10% at room temperature ("non-polar organic solvents"). Suitable solvents for the Precipitation process are polar organic solvents that are miscible with the anti-solvent, which is water.

Examples of polar and non polar organic solvents are those listed below.

Suitable polar organic solvents include, but are not limited to:
1. $C_1$-$C_4$-Alkanols such as methanol, ethanol, n-propanol or isopropanol;
2. Amides, N-methylamides and N,N-dimethylamides of $C_1$-$C_3$-carboxylic acids such as formamide, dimethylformamide (DMF), acetamide and N,N-dimethylacetamide;

3. 5 or 6-membered lactames with a total of 7 carbon atoms such as pyrrolidone, N-methylpyrrolidone, N-ethylpyrrolidone, N-isopropylpyrrolidone, N-hydroxyethylpyrrolidone;
4. Dimethylsulfoxid and sulfolane;
5. Ketones with 3 to 6 carbon atoms such as acetone, 2-butanone, cyclopentanone and cyclohexanone;
6. Acetonitrile;
7. 5- or 6-membered lactones such as γ-butyrolactone;
8. Polyols and polyetherols such as glycol, glycerin, dimethoxyethan, ethylendiglycol, ethylenglycolmonomethylether, etc;
9. Cyclic carbonates having 3 to 5 carbon atoms including propylene carbonate and ethylene carbonate; and
10. Dimethyl (poly)$C_2$-$C_3$-alkyleneglycol ethers such as dimethoxyethane, diethyleneglycoldimethylether, triethyleneglycoldimethylether, dipropyleneglycoldimethylether, low molecular weight polyethyleneglycoles and low molecular weight polypropyleneglycoles (MW≤400).

More preference is given to organic solvents of the group 1, and to their mixtures with water. In the mixtures with water the relative amount of organic solvent and water may vary from 2:1 to 1:200 (v/v), in particular from 1:5 to 1:100 (v/v).

An especially suitable polar organic solvent to be used alone or in mixture with water is an alcohol as mentioned above ($C_1$-$C_4$-alkanols such as methanol, ethanol, n-propanol or isopropanol)

Example of non-polar solvents include, but are not limited to $C_8$ to $C_{11}$ aromatic petroleum derivatives (aromatic hydrocarbons) with a solubility in water <0.1% (w/w) and a distillation range from 130° C. to 300° C. (commercial available under the following brand names: Solvesso 100, Solvesso 150, Solvesso 200, Solvesso 150ND, solvesso 200ND, Aromatic 150, Aromatic 200, Hydrosol A 200, Hydrosol A 230/270, Caromax 20, Caromax 28, Aromat K 150, Aromat K 200, Shellsol A 150, Shellsol A 100, Fin FASTX 150, Fin FAS-TX 200), vegetable oils such as coco oil, palm kern oil, palm oil, soya oil, rapeseed oil, corn oil and the methyl or ethyl esters of the afore-mentioned oils, hydrocarbons such as aromatic depleted, linear paraffinic, isoparaffinic, cycloparaffinic having a flash point between 40° C. and 250° C. and a distillation range from 150° C. to 450° C.

b) As set forth above, in the "Shear process", the complex is obtained by applying shear forces to the two components of the co-crystal.

In this process, pesticide II and 4-hydroxybenzoic are combined in a suitable solvent provided, however, that the pesticide II and 4-hydroxybeonzoic acid are not dissolved and still in the solid stage. Principally, it is also possible to combine pesticide II and 4-hydroxybeonzoic acid in a solid stage without any solvent and applying shear forces afterwards to the thus obtained solid mixture. Suspending in a suitable solvent is preferred.

Applying shear forces to the thus obtained suspension is preferably performed at a temperature of at least 15° C., frequently at a temperature of at least 20° C., preferably at a temperature of at least 30° C., in particular of at least 35° C., e.g. from 15° C. to 80° C., wherein the upper limit depends on the melting point of the pesticide II. 4-

However, it is not necessary for pesticide II to be solid during the process and it might be advantageous if the temperature is close to or above the melting point of pesticide II. Upon applying shear forces to the liquid mixture at elevated temperatures the formation of the crystalline complex might be accelerated.

The amount of the solvent in the suspension, which is obtained by combining 4-hydroxybenzoic acid and pesticide II in the suitable solvent, is between 5 and 50-w %, preferably in between 5 and 30 w/w %, based on the total weight of the thus obtained suspension.

The suspension may contain 4-hydroxybenzoic acid and pesticide II in a relative molar ratio varying from 1:5 to 20:1, preferably from 1:1.2 to 15:1. If one of the components is in excess with regard to the stoichiometry of the crystalline complex, a mixture of the crystalline complex and the compound being in excess will be obtained. For formulation purposes, the presence of an excess of 4-hydroxybenzoic or pesticide II might be acceptable. In particular the presence of an excess of 4-hydroxybenzoic does not cause stability problems. However, it is preferred, that the amount of pesticide II in the aqueous suspension does not exceed more than 20 mol-% by weight, in particular not more than 10 mol-%, based on the amount of 4-hydroxybenzoic present in the mixture. Therefore, the present invention relates in particular to aqueous formulations containing the crystalline complex of the present invention, provided that, if one or both of 4-hydroxybenzoic acid and pesticide II are present in the formulation in non-complexed form, the amount of the non-complexed pesticide II does not exceed 20 mol-%, in particular 10 mol-% in the formulation.

The time required for formation of the crystalline complex depends in a manner known per se on the applied shear and the temperature and can be determined by the person skilled in the art in standard experiments. Times in the range of e.g. from 10 min. to 48 hours have been found to be suitable for formation of the crystalline complex in the aqueous suspension containing 4-hydroxybenzoic acid and pesticide II, although a longer period of time is also conceivable. A shearing time of 0.5 to 24 hours is preferred.

In a preferred embodiment, shear forces are applied to the aqueous suspension of pesticide II and 4-hydroxybenzoic, which is obtained by combining 4-hydroxybenzoic acid and pesticide II in the aqueous liquid. Shear forces can be applied by suitable techniques, which are capable of providing sufficient shear to bring the particles of 4-hydroxybenzoic acid and pesticide II into an intimate contact and/or to comminute the particles of the crystalline complex. Suitable techniques include grinding, crushing or milling, in particular by wet grinding or wet milling, including e.g. bead milling or by use of a colloid mill. Suitable shearing devices include in particular ball mills or bead mills, agitator ball mills, circulating mills (agitator ball mills with pin grinding system), disk mills, annular chamber mills, double cone mills, triple roll mills, batch mills, colloid mills, and media mills, such as sand mills. To dissipate the heat energy introduced during the grinding process, the grinding chambers are preferably fitted with cooling systems. Particularly suitable is the ball mill Drais Superflow DCP SF 12 from DRAISWERKE, INC. 40 Whitney Road. Mahwah, N.J. 07430 USA, a Drais Perl Mill PMC from DRAISWERKE, INC., the circulating mill system ZETA from Netzsch-Feinmahltechnik GmbH, the disk mill from Netzsch Feinmahltechnik GmbH, Selb, Germany, the bead mill Eiger Mini 50 from Eiger Machinery, Inc., 888 East Belvidere Rd., Grayslake, Ill. 60030 USA and the bead mill DYNO-Mill KDL from WA Bachofen AG, Switzerland. However, other homogenizers might also be suitable, including high shear stirrers, Ultra-Turrax apparatus, static mixers, e.g. systems having mixing nozzles and other homogenizers such as colloid mills.

In a preferred embodiment of the invention, shear forces are applied by bead milling. In particular, bead sizes in the range of from 0.05 to 5 mm, more particularly from 0.2 to 2.5 mm, and most particularly from 0.5 to 1.5 mm have been found to be suitable. In general, bead loadings in the range of from 40 to 99%, particularly from 70 to 97%, and more particularly from 65 to 95% may be used.

Preferred solvents for the Shear process are polar organic solvents or mixtures of water and at least one polar organic solvent for the slurry process are those, which are at least partially water miscible, i.e. which have miscibility with water of at least 10% v/v, more preferably at least 20% v/v at room temperature, mixtures thereof and mixtures of said water miscible solvents with organic solvents that have miscibility with water of less than 10% v/v at room temperature. Preferably the organic solvent comprises at least 80% v/v, based on the total amount of organic solvent, of the at least one water miscible solvent.

Suitable solvents having a water miscibility of at least 10% at room temperature include, but are not limited to the polar organic solvents as defined above.

More preference is given to organic solvents of the group 1, and to their mixtures with water. In the mixtures with water the relative amount of organic solvent and water may vary from 2:1 to 1:200 (v/v), in particular from 1:5 to 1:100 (v/v).

An especially suitable polar organic solvent to be used alone or in mixture with water is an alcohol as mentioned above ($C_1$-$C_4$-alkanols such as methanol, ethanol, n-propanol or isopropanol).

c) In the Slurry process, the complex is obtained from a slurry of 4-hydroxybenzoic acid and pesticide II in a solvent comprising an organic solvent or in particular from a slurry of 4-hydroxybenzoic acid and pesticide II in a mixture of water and organic solvent. Consequently, this method comprises suspending 4-hydroxybenzoic acid and pesticide II in an organic solvent or in a mixture of water and organic solvent.

Preferred organic solvents or mixtures of water and organic solvent for the slurry process are those, where 4-hydroxybenzoic acid and pesticide II have a comparable solubility. Comparable solubility means that the solubilities of the individual compounds in the solvent or solvent system differ by a factor of not more than 20, in particular by a factor of not more than 10. It is, however, also possible to use a solvent or solvent system, wherein the solubilities of the individual compounds are not comparable. In this case, it might be preferable to use the compound having the higher solubility in the respective solvent or solvent system in excess.

Preferred solvents for the slurry process are those, which are at least partially water miscible, i.e. which have miscibility with water of at least 10% v/v, more preferably at least 20% v/v at room temperature, mixtures thereof and mixtures of said water miscible solvents with organic solvents that have miscibility with water of less than 10% v/v at room temperature. Preferably the organic solvent comprises at least 80% v/v, based on the total amount of organic solvent, of the at least one water miscible solvent.

Suitable solvents are polar organic solvents as defined above.

More preference is given to organic solvents of the group 1, and to their mixtures with water. In the mixtures with water the relative amount of organic solvent and water may vary from 2:1 to 1:200 (v/v), in particular from 1:5 to 1:100 (v/v).

An especially suitable organic solvent to be used alone or in mixture with water is an acochol as mentioned above ($C_1$-$C_4$-alkanols such as methanol, ethanol, n-propanol or isopropanol).

The slurry process can by simply performed by suspending 4-hydroxybenzoic acid and pesticide II in the organic solvent or in a solvent/water mixture. The relative amounts of 4-hydroxybenzoic acid and pesticide II and solvent or solvent/water mixture will be chosen to obtain a suspension at the given temperature. Complete dissolution of 4-hydroxybenzoic acid and pesticide II should be avoided. In particular, 4-hydroxybenzoic acid and pesticide II are suspended in an amount from 1 to 500 g, more preferably 10 to 400 g per liter of solvent or solvent/water mixture.

The relative molar amount of 4-hydroxybenzoic acid and pesticide II in the slurry process may vary from 1:100 to 100:1, preferably from 1:10 to 10:1, depending on the relative solubilities of 4-hydroxybenzoic acid and pesticide II in the chosen solvent or solvent system. In solvent systems where the solubilities of the pure 4-hydroxybenzoic acid and pesticide II are comparable the preferred molar ratio is from 2:1 to 1:2, in particular from 1.5:1 to 1:1.5 and especially about 1:1 (i.e. from 1.1:1 to 1:1.1). An excess of pesticide II will be used in solvent systems where pesticide II has a higher solubility. This applies also vice versa with 4-hydroxybenzoic. If one of the components is in excess with regard to the stoichiometry of the crystalline complex, a mixture of the crystalline complex and the compound being in excess might be obtained, though an excess might also remain dissolved in the mother liquor, in particular if the compound which is used in excess has a high solubility in the chosen solvent system. For formulation purposes, the presence of an excess of pesticide II or 4-hydroxybenzoic might be acceptable. In particular the presence of an excess of 4-hydroxybenzoic does not cause stability problems. For preparing the pure crystalline complex, 4-hydroxybenzoic acid and pesticide II will be used in a relative molar amount which is close to the stoichiometry of the complex to be formed and which usually will not deviate more than 50 mol.-%, based on the stoichiometrically required amount.

The slurry process is usually performed at a temperature of at least 5° C., preferably at least 10° C. and in particular at least 20° C., e.g. from 5 to 80° C., preferably from 10 to 55° C., in particular from 20 to 40° C.

The time required for formation of the crystalline complex by the slurry process depends on the temperature, the type of solvent and is generally 1 h. In any case, complete conversion is achieved after one week, however, the complete conversion will usually require not more than 24 h.

According to one embodiment of the invention the slurry process is performed in the presence of co-crystals of 4-hydroxybenzoic acid and pesticide II as seeding crystals. Usually 0.01 to 10% by weight, preferably 0.1 to 5% and more preferably 0.3 to 2% by weight of seeding crystals are employed based on the combined weight of 4-hydroxybenzoic acid and pesticide II.

As already mentioned above, the crystalline complex as defined herein are suitable for preparing crop protection compositions based on solid pesticides, such as aqueous suspension concentrates (SC, FS), suspo-emulsions (SE) and water dispersable granules (WG), water-dispersible powders (WP, WS), Dustable powders (DP, DS), granules (GR, FG, GG, MG), Dispersible concentrates (DC) and in particular for preparing a SC, FS, SE or WG formulation.

Accordingly, the invention also provides an agricultural composition for crop protection, comprising complex I or II or III or IV or V or VI as defined herein, and if appropriate if appropriate, further customary formulation auxiliaries.

The term formulation auxiliaries includes, but is not limited to liquid and solid carriers and further auxiliaries such as surfactants (adjuvants, wtters, tackifiers, dispersants or emulsifiers), furthermore viscosity-modifying additives (thickeners), antifoam agents, antifreeze agents, agents for adjusting the pH, stabilizers, anticaking agents and biocides (preservatives). Further auxiliaries suitable for seed treatment formulations comprise colorants, stickers, fillers, and plasticizers.

The weight ratios of formulation auxiliaries and the respective crystalline complex lie in ranges typically used for the respective solid formulation and the SE or SC formulation.

For example, in SCs and SEs, the amount of the crystalline complex and, if appropriate, further active compounds is usually in the range from 10 to 70% by weight, in particular in the range from 15 to 50% by weight, based on the total weight of the suspension concentrate or suspo-emulsion.

In the other solid formulations (WG, WP, WS, DP, DS, GR, FG, GG, MG, DC), the amount of the crystalline complex and, if appropriate, further active compounds is usually in the range from 10 to 90% by weight, in particular in the range from 15 to 70% by weight, based on the total weight of the solid formulation.

The total amount of formulation auxiliaries depends on the type of formulation used. Generally, it varies from 10 to 90% by weight, in particular from 85 to 30% by weight based on the total weight of the formulation.

The amount of surfactants varies depending on the formulation type. Usually, it is in the range from 0.1 to 20% by weight, in particular from 0.2 to 15% by weight and particularly preferably from 0.5 to 10% by weight based on the total weight of the formulation.

The amount of carriers (liquid or solid) varies depending on the formulation type. Usually, it is in the range from 1 to 90% by weight, in particular from 10 to 60% by weight and particularly preferably from 15 to 50% by weight based on the total weight of the formulation.

The amount of the remaining formulation auxiliaries (viscosity-modifying additives (thickeners), antifoam agents, antifreeze agents, agents for adjusting the pH, stabilizers, anticaking agents and biocides (preservatives), colorants, stickers, fillers, and plasticizers) varies depending on the formulation type. Usually, it is in the range from 0.1 to 60% by weight, in particular from 0.5 to 40% by weight and particularly preferably from 1 to 20% by weight based on the total weight of the formulation.

Suitable liquid carriers are water, optionally containing water-miscible organic solvents, such as those of groups 1 to 10, and also organic solvents in which the crystalline complex I, II, III, IV, V or VI has low or no solubility, for example those in which the solubility of the crystalline complex I, II, III, IV or VI has at 25° C. and 1013 mbar are not more than 1% by weight, in particular not more than 0.5% by weight and especially not more than 0.1% by weight.

Examples of solvents (particularly useful for SE formulations) are organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, terpenes (including, but not limited to d-limonene) alkylated naphthalenes or their derivatives, linear and branched alcohols such as propanol, butanol, cyclohexanol, 2-phenoxyethanol, dodecylphenol, benzylalkohol, glycols, ketones such as cyclohexanone, 2-heptanone, acetophenone, 4-methoxyacetophenone, methylisoamylketone, methylisobutylketone, fatty acid dimethylamides, fatty acids and fatty acid esters, esters such as 2-ethylhexyl acetate, butylene carbonate, isobornyl acetate, dimethyl succinate, dimethyl adipate, dimethyl glutarate, diisobutyl succinate, diisobutyl adipate, diisobutyl glutarate (and also mixtures of esters, e.g. mixtures of dimethyl succinate, dimethyl adipate, dimethyl glutarate, e.g. commercially available as Rhodiasolv RPDE; or mixtures of diisobutyl succinate, diisobutyl adipate, diisobutyl glutarate e.g. commercially available as Rhodiasolv RPDE Rhodiasolv DIB), -and strongly polar solvents, e.g. amines such as N-octylpyrrolidon and mixtures thereof.

Suitable solid carriers are, in principle, all solid substances usually used in crop protection compositions, in particular in fungicides. Solid carriers are, for example, mineral earths, such as silica gels, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Preferred surfactants are anionic and non-ionic surfactants (emulsifiers). Suitable surfactants are also protective colloids.

Suitable surfactants (adjuvants, wtters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalenesulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Viscosity-modifying additives (thickeners) are compounds that impart a modified flowability to compositions, i.e. high viscosity under static conditions and low viscosity during agitation). Examples of suitable thickeners are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). (added at 0.005-10%, 0.01-5%, or 0.02-2%) Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Preservatives (bactericides) may be added for stabilizing the suspension concentrates according to the invention. Suitable preservatives are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Suitable antifreeze agents are liquid polyols, for example ethylene glycol, propylene glycol or glycerol.

If appropriate, the water dispersable granules (WG), water-dispersible powders (WP, WS), Dustable powders (DP, DS), granules (GR, FG, GG, MG), Dispersible concentrates (DC), in particular in the WG, SCs or SEs according to the invention may comprise buffers for regulating the pH. Examples of buffers are alkali metal salts of weak inorganic or organic acids, such as, for example, phosphoric acid, boric acid, acetic acid, propionic acid, citric acid, fumaric acid, tartaric acid, oxalic acid and succinic acid.

If the formulations of the crystalline complexes are used for seed treatment, they may comprise further customary components as employed in the seed treatment, e.g. in dressing or coating. Examples are in particular colorants, stickers, fillers, and plasticizers besides the above-mentioned components.

Colorants are all dyes and pigments which are customary for such purposes. In this context, both pigments, which are sparingly soluble in water, and dyes, which are soluble in water, may be used. Examples which may be mentioned are the dyes and pigments known under the names Rhodamin B, C. I. Pigment Red 112 and C. I. Solvent Red 1, Pigment blue 15:4, Pigment blue 15:3, Pigment blue 15:2, Pigment blue 15:1, Pigment blue 80, Pigment yellow 1, Pigment yellow 13, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108. The amount of colorants will usually not exceed 20% by weight of the formulation and preferably ranges from 0.1 to 15% by weight, based on the total weight of the formulation.

Stickers are all customary binders which can be employed in dressing products. Examples of suitable binders comprise thermoplastic polymers such as polyvinylpyrrolidone, polyvinyl acetate, polyvinyl alcohol and tylose, furthermore polyacrylates, polymethacrylates, polybutenes, polyisobutenes, polystyrene, polyethylenamines, polyethylenamides, the aforementioned protective colloids, polyesters, polyetheresters, polyanhydrides, polyesterurethanes, polyesteramides, thermoplastic polysaccharides, e.g. cellulose derivates such as celluloseesters, celluloseethers, celluloseetheresters including methylcellulose, ethylcellullose, hydroxymethylcellulose, carboxymethylcellulose, hydroxypropylcellulose and starch derivatives and modified starches, dextrines, maltodextrines, alginates and chitosanes, moreover fats, oils, proteins, including casein, gelatin and zeins, gum arabics, shellacs. Preferred stickers are biocompatible, i.e. they do not have a noticeable phytotoxic activity. Preferably the stickers are biodegradable. Preferably the sticker is chosen that it acts as a matrix for the active ingredients of the formulation. The amount of stickers will usually not exceed 40% by weight of the formulation and preferably ranges from 1 to 40% by weight, and in particular in the range from 5 to 30% by weight, based on the total weight of the formulation.

In general, the respective solid formulations, in particular the SC, SE or WG comprise the crystalline complex in a finely divided particulate form. In SC- and SE-formulations the particles of the crystalline complex are suspended in a liquid medium, preferably in an aqueous medium. In water dispersable granules (WG), water-dispersible powders (WP, WS), Dustable powders (DP, DS), granules (GR, FG, GG, MG), Dispersible concentrates (DC), in particular in the WG, the finely divided particles are loosely agglomerated into larger granules that disintegrate upon dilution in water and then lead to a suspension of these finely divided particles. The size of the active compound particles, i.e. the size which is not exceeded by 90% by weight of the active compound particles, is typically not more than 30 µm, preferably not more than 20 µm, in particular not more than 10 µm, especially not more than 5 µm, as determined by dynamic light scattering. Advantageously, at least 40% by weight and in particular at least 60% by weight of the particles in the SCs according to the invention have diameters below 2 µm.

The respective formulations can be prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095, 558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

For example, suspension concentrates, in particular aqueous suspension concentrates can be prepared by suspending the crystalline complex in a suitable liquid carrier, which may contain conventional formulation additives as described hereinafter. However, it is preferred to prepare the suspension concentrate by the shear process as described herein, i.e. by applying shear forces to a liquid which contains suspended particles of 4-hydroxybenzoic acid and pyraclostrobin and optionally further additives until the crystalline complex has been formed.

Suspo-emulsions can be prepared in accordance with the methods as described for SCs with the provisoe that a second pesticide (besides the crystalline complex) can be added to the final SC or during preparation of the SC solubilised in a suitable organic solvent (optionally together with suitable further formulation auxiliaries).

Powders, materials for spreading and dustable products can be prepared by mixing or concomitantly grinding the crystalline complex (and optionally a further pesticide) with a solid carrier.

Granules, for example coated granules, impregnated granules and homogeneous granules, can be prepared by binding the active compounds to solid carriers.

Powders, materials for spreading and dusts can be prepared by mixing or concomitantly grinding the compounds I and, if appropriate, further active substances, with at least one solid carrier.

Granules, e.g. coated granules, impregnated granules and homogeneous granules, can be prepared by binding the active substances to solid carriers.

The formulations as described above may also comprise further active compounds against pests. For example, insecticides or further herbicides or fungicides or else herbicidal or growth-regulating active compounds or fertilizers can be added as further active components according to need.

All embodiments of the formulations comprising at least one crystalline complex are hereinbelow referred to as "agrochemical formulation".

The present invention comprises a method for controlling phytopathogenic fungi, wherein the phytopathogenic fungi, their habitat, breeding grounds, their locus or the plants to be protected against phytopathogenic fungi, the soil or plant propagation material are treated with an effective amount of the crystalline complex I, II, III or IV or with an agricultural formulation comprising at least one complex I, II, III or IV.

The present invention furthermore comprises a method for improving the health of plants, wherein the plant, the locus where the plant is growing or is expected to grow or plant propagation material from which the plant grows are treated with an effective amount of the crystalline complex I, II or IV or with an agricultural formulation comprising at least one complex I, II or IV.

The present invention furthermore comprises a method of combating pests, which are, depending on the pesticide II either phytopathogenic fungi or harmful insects, which comprises contacting plant propagation material (preferably seed) to be protected from attack or infestation by said phytopathogenic pests with an effective amount of a agrochemical formulation comprising at least one crystalline complex I, II, III, VII or IV.

The invention also relates to the propagation products of plants, and especially the seed comprising, that is, coated with and/or containing, a complex I, II, III, VII or IV preferably or a agrochemical formulation containing at least one aforementioned crystalline complexes. The plant propagation material (preferably seed) comprises the inventive mixtures in an amount of from 0.01 g to 10 kg per 100 kg of plant propagation material (preferably seed).

If the method is defined as a method of combating phytopathogenic pests or increasing the health of plants, wherein
a. the phytopathogenic pests, their habitat, breeding grounds, their locus or the plants to be protected or the soil; or
b. the plant, the locus where the plant is growing or is expected to grow;
are treated with an effective amount of the respective crystalline complex or with an agricultural formulation comprising at the respective complex, the amounts of crystalline complex is, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

If the method is defined as a method, wherein the plant propagation material
(a) the pest, their habitat, breeding grounds, their locus or the plants to be protected against pest attack or the soil; or
(b) the plant, the locus where the plant is growing or is expected to grow;
are treated with an effective amount of the respective crystalline complex or with an agricultural formulation comprising at least one complex, the amounts of crystalline complex is, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

The term phytopathogenic fungi includes, but is not limited to the following plant diseases: *Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternate*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuceliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; *Esca* (dieback, apoplexy) on vines, caused by *Formitiporia* (syn. *Phellinus*) *punctata*, *F. mediterranea*, *Phaeomoniella chlamydospora* (earlier *Phaeo acremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e.g. *G. sabinae* (rust) on pears; *Helmintho sporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (e.g. *P. paraonions* (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g.

on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*); *Pyrenophora* (anamorph: *Drechslera*) *tritici*-repentis (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collocygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalls* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversy* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The agrochemical formulations comprising at least one crystalline complex I, II, III or IV can therefore be used for the control of a multitude of phytopaghogenic fungi or insects on various cultivated plants, such as wheat, rye, barley, oats, rice, corn, grass, bananas, cotton, soya, coffee, sugar cane, vines, fruits and ornamental plants, and vegetables, such as cucumbers, beans, tomatoes, potatoes and cucurbits, and on the seeds of these plants.

The term harml insects refers to animal pests from the following orders:

insects from the order of the lepidopterans (Lepidoptera), for example *Agrotis ipsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae,*

*Ortiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus similis, Tipula* oleracea, and *Tipula paludosa* thrips (Thysanoptera), e.g. *Dichromothrips corbetti, Dichromothrips* ssp, *Frankliniella fusca, Frankliniella occidentalis, Frankliniella tritici, Scirtothrips citri, Thrips oryzae, Thrips palmi* and *Thrips tabaci*, termites (Isoptera), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis*, true bugs (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges lards, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphum rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus*.

ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile*, crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina*, Arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis*; Araneida, e.g. *Latrodectus mactans,* and *Loxosceles reclusa*, fleas (Siphonaptera), e.g. *Ctenocephalides felis, Ctenocephalides canis, Xenopsylla cheopis, Pulex irritans, Tunga penetrans,* and *Nosopsyllus fasciatus*, silverfish, firebrat (Thysanura), e.g. *Lepisma saccharina* and *Thermobia domestica*, centipedes (Chilopoda), e.g. *Scutigera coleoptrata*, millipedes (Diplopoda), e.g. *Narceus* spp., Earwigs (Dermaptera), e.g. *forficula auricularia*, lice (Phthiraptera), e.g. *Pediculus humanus* capitis, *Pediculus humanus* corporis, *Pthirus pubis, Haematopinus eurysternus, Haematopinus suis, Linognathus vituli, Bovicola bovis, Menopon gallinae, Menacanthus stramineus* and *Solenopotes capillatus*, plant parasitic nematodes such as root-knot nematodes, *Meloidogyne arenaria, Meloidogyne chitwoodi, Meloid-*

*ogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolii,* and other *Heterodera* species; seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenchus* species; ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species; sheath nematodes, *Hemicycliophora* species and *Hemicriconemoides* species; *Hirshmanniella* species; lance nematodes, *Hoplolaimus columbus, Hoplolaimus galeatus* and other *Hoplolaimus* species; false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scribneri, Pratylenchus vulnus, Pratylenchus zeae* and other *Pratylenchus* species; *Radinaphelenchus cocophilus* and other *Radinaphelenchus* species; burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species; stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudatum* and other *Xiphinema* species; and other plant parasitic nematode species.

The present invention furthermore comprises a method of improving the health of plants, which comprises applying a an effective amount of a agrochemical formulation comprising at least one crystalline complex I, II, III, VII or IV, to plants, parts of plants, plant propagation material or the locus where plants grow.

Herein, the amounts of crystalline complex is, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The present invention furthermore comprises a method of controlling undesired vegetation, which comprises allowing a herbicidally effective amount of comprising at least one crystalline complex V or VI to act on plants, their habitat or on the locus, where the plant grows.

The control of undesired vegetation is understood as meaning the destruction of weeds. Weeds, in the broadest sense, are understood as meaning all those plants which grow in locations where they are undesired, for example:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

Generally the term "plants" also includes plants which have been modified by breeding, mutagenesis or genetic engineering (transgenic and non-transgenic plants). Genetically modified plants are plants, which genetic material has been modified by the use of recombinant DNA techniques in a way that it cannot readily be obtained by cross breeding under natural circumstances, mutations or natural recombination.

Plants and as well as the propagation material of said plants, which can be treated with crystalline complex Complex I, II, III, IV, V, VI or VII include all modified non-transgenic plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, crystalline complex I, II, III, IV, V, VI or VII can be applied in accordance with the methods of treatment as set forth above also to plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein (s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides. Tolerance to herbicides can be obtained by creating insensitivity at the site of action of the herbicide by expression of a target enzyme which is resistant to herbicide; rapid metabolism (conjugation or degradation) of the herbicide by expression of enzymes which inactivate herbicide; or poor uptake and translocation of the herbicide. Examples are the expression of enzymes which are tolerant to the herbicide in comparison to wild type enzymes, such as the expression of 5-enolpyruvylshikimate-3-phosphate synthase (EPSPS), which is tolerant to glyphosate (see e.g. Heck et. al, Crop Sci. 45, 2005, 329-339; Funke et. al, PNAS 103, 2006, 13010-13015; U.S. Pat. No. 5,188,642, U.S. Pat. No. 4,940,835, U.S. Pat. No. 5,633,435, U.S. Pat. No. 5,804,425, U.S. Pat. No. 5,627,061), the expression of glutamine synthase, which is tolerant to glufosinate and bialaphos (see e.g. U.S. Pat. No. 5,646,024, U.S. Pat. No. 5,561,236) and DNA constructs coding for dicamba-degrading enzymes (see for general reference US 2009/0105077, e.g. U.S. Pat. No. 7,105,724 for dicamba resistaince in bean, maize (for maize see also WO2008051633), cotton (for cotton see also U.S. Pat. No. 5,670,454), pea, potatoe, sorghum, soybean (for soybean see also U.S. Pat. No. 5,670,454), sunflower, tobacco, tomato (for tomato see also U.S. Pat. No. 5,670,454)).

Furthermore, this comprises also plants tolerant to applications of imidazolinone herbicides (canola (Tan et. al, Pest Manag. Sci 61, 246-257 (2005)); maize (U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100, Tan et. al, Pest Manag. Sci 61, 246-257 (2005)); rice (U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100, S653N (see e.g. US 2003/0217381), S654K (see e.g. US 2003/0217381), A122T (see e.g. WO 04/106529) S653 (At)N, S654 (At)K, A122 (At)T and other resistant rice plants as described in WO0027182, WO 05/20673 and WO0185970 or U.S. Pat. No. 5,545,822, U.S. Pat. No. 5,736,629, U.S. Pat. No. 5,773,703, U.S. Pat. No. 5,773,704, U.S. Pat. No. 5,952,553, U.S. Pat. No. 6,274,796); millet (U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100); barley (U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100); wheat (U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439, U.S. Pat. No. 6,222,100, WO 04/106529, WO 04/16073, WO 03/14357, WO 03/13225 and WO 03/14356); sorghum (U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100); oats (U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100); rye (U.S. Pat. No. 4,761,373, U.S. Pat. No. 5,304,732, U.S. Pat. No. 5,331,107, U.S. Pat. No. 5,718,079, U.S. Pat. No. 6,211,438, U.S. Pat. No. 6,211,439 and U.S. Pat. No. 6,222,100); sugar beet (WO9802526/WO9802527); lentils (US2004/0187178); sunflowers (Tan et. al, Pest Manag. Sci 61, 246-257 (2005))). Gene constructs can be obtained, for example, from micro-organism or plants, which are tolerant to said herbicides, such as the *Agrobacterium* strain CP4 EPSPS which is resistant to glyphosate; *Streptomyces* bacteria which are resistance to glufosinate; *Arabidopsis, Daucus carotte, Pseudomonoas* sp. or *Zea mais* with chimeric gene sequences coging for HDDP (see e.g. WO 1996/38567, WO 2004/55191); *Arabidopsis thaliana* which is resistant to protox inhibitors (see e.g. US2002/0073443).

Examples of commercial available plants with tolerance to herbicides, are the corn varieties "Roundup Ready Corn", "Roundup Ready 2" (Monsanto), "Agrisure GT", "Agrisure GT/CB/LL", "Agrisure GT/RW", "Agrisure 3000GT" (Syngenta), "YieldGard VT Rootworm/RR2" and "YieldGard VT Triple" (Monsanto) with tolerance to glyphosate; the corn varieties "Liberty Link" (Bayer), "Herculex I", "Herculex RW", "Herculex Xtra" (Dow, Pioneer), "Agrisure GT/CB/LL" and "Agrisure CB/LL/RW" (Syngenta) with tolerance to glufosinate; the soybean varieties "Roundup Ready Soybean" (Monsanto) and "Optimum GAT" (DuPont, Pioneer) with tolerance to glyphosate; the cotton varieties "Roundup Ready Cotton" and "Roundup Ready Flex" (Monsanto) with tolerance to glyphosate; the cotton variety "FiberMax Liberty Link" (Bayer) with tolerance to glufosinate; the cotton variety "BXN" (Calgene) with tolerance to bromoxynil; the canola varieties "Navigator" and "Compass" (Rhone-Poulenc) with bromoxynil tolerance; the canola varierty "Roundup Ready Canola" (Monsanto) with glyphosate tolerance; the canola variety "InVigor" (Bayer) with glufosinate tolerance; the rice variety "Liberty Link Rice" (Bayer) with glufosinate tolerance and the alfalfa variety "Roundup Ready Alfalfa" with glyphosate tolerance. Further modified plants with herbicide are commonly known, for instance alfalfa, apple, *eucalyptus*, flax, grape, lentils, oil seed rape, peas, potato, rice, sugar beet, sunflower, tobacco, tomatom turf grass and wheat with tolerance to glyphosate (see e.g. U.S. Pat. No. 5,188,642, U.S. Pat. No. 4,940,835, U.S. Pat. No. 5,633,435, U.S. Pat. No. 5,804,425, U.S. Pat. No. 5,627,061); beans, soybean, cotton, peas, potato, sunflower, tomato, tobacco, corn, sorghum and sugarcane with tolerance to dicamba (see e.g. US 2009/0105077, U.S. Pat. No. 7,105,724 and U.S. Pat. No. 5,670,454); pepper, apple, tomato, hirse, sunflower, tobacco, potato, corn, cucumber, wheat, soybean and sorghum with tolerance to 2,4-D (see e.g. U.S. Pat. No. 6,153,401, U.S. Pat. No. 6,100,446, WO2005107437, U.S. Pat. No. 5,608,147 and U.S. Pat. No. 5,670,454); sugarbeet, potato, tomato and tobacco with tolerance to glyphosinate (see e.g. U.S. Pat. No. 5,646,024, U.S. Pat. No. 5,561,236); canola, barley, cotton, *juncea*, lettuce, lentils, melon, millet, oats, oilseed rapre, potato, rice, rye, sorghum, soybean, sugarbeet, sunflower, tobacco, tomato and wheat with tolerance to acetolactate synthase (ALS) inhibiting herbicides, such as triazolopyrimidine sulfonamides, growth inhibitors and imidazolinones (see e.g. U.S. Pat. No. 5,013,659, WO2006060634, U.S. Pat. No. 4,761,373, U.S. Pat. No. 5,304,732, U.S. Pat. No. 6,211,438, U.S. Pat. No. 6,211,439 and U.S. Pat. No. 6,222,100); cereal, sugar cane, rice, corn, tobacco, soybean, cotton, rapeseed, sugar beet and potato with tolerance to HPPD inhibitor herbicides (see e.g. WO2004/055191, WO199638567, WO1997049816 and U.S. Pat. No. 6,791,014); wheat, soybean, cotton, sugar beet, rape, rice, corn, sorghum and sugar cane with tolerance to protoporphyrinogen oxidase (PPO) inhibitor herbicides (see e.g. US2002/0073443, US20080052798, Pest Management Science, 61, 2005, 277-285). The methods of producing such herbicide resistant plants are generally known to the person skilled in the art and are described, for example, in the publications mentioned above.

Further examples of commercial available modified plants with tolerance to herbicides "CLEARFIELD Corn", "CLEARFIELD Canola", "CLEARFIELD Rice", "CLEARFIELD Lentils", "CLEARFIELD Sunlowers" (BASF) with tolerance to the imidazolinone herbicides.

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the CryIAb toxin), YieldGard® Plus (corn cultivars producing CryIAb and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the CryIAc toxin), Bollgard® I (cotton cultivars producing the CryIAc toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); BtXtra®, NatureGard®, KnockOut®, BiteGard®, Protecta®, Bt11 (e.g. Agrisure® CB) and Bt176 from Syngenta Seeds SAS, France, (corn cultivars producing the CryIAb toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the CryIAc toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

Particularly preferred modified plants suitable to be used in the methods of the present invention related to complex V and VI are those, which are rendered tolerant to herbicides, in particular tolerant to imidazolinone herbicides, most preferably those imidazolinone resistant plants set forth above.

The figures and examples below serve to illustrate the invention and are not to be understood as limiting it.

FIGURES

FIG. 1. PXRD of Complex I (pyraclostrobin: 4-hydroxy benzoic acid)

FIG. 2. PXRD of Complex II, (epoxiconazol 4-hydroxy benzoic acid)

FIG. 3. PXRD of Complex III, (tebuconazol: 4-hydroxy benzoic acid)

FIG. 4. PXRD of Complex IV, (boscalid: 4-hydroxy benzoic acid)

FIG. 5. PXRD of Complex V (imazethapyr: 4-hydroxy benzoic acid)

FIG. 6. PXRD of Complex VI (imazamox: 4-hydroxy benzoic acid)

FIG. 7. PXRD of Complex VII (acetamiprid: 4-hydroxy benzoic acid)

FIG. 8. DSC-trace of Complex I
FIG. 9. DSC-trace of Complex II
FIG. 10. DSC-trace of Complex III
FIG. 11. DSC-trace of Complex IV
FIG. 12. DSC-trace of Complex VII

EXAMPLES

A) Preparation

Example 1

Complex I

For a 1:1 co-crystal of pyraclostrobin and 4-hydroxi benzoic acid, 100.0 mg of pyraclostrobin, 35.6 mg of 4-hydroxi benzoic acid and 100 µl of 50 v/v-% water-ethanol solution was grinded in a ball mill (Retsch Modell MM301) for 15 minutes. The residual solvents were left to dry in air. The crystalline product gave the PXRD presented in FIG. 1.

Example 2

Complex I

For a 1:1 co-crystal of pyrachlostrobin and 4-hydroxi benzoic acid, 100.2 mg of pyrachlostrobin, 35.6 mg of 4-hydroxi benzoic acid were placed in a 10 ml glass vial and dissolved in 4 ml of MeOH at 40° C. to give a clear solution. The solution was left to evaporate at RT in the open vial. After all of the solvent had evaporated, one crystal was selected for single crystal structure determination. The crystalline product gave the PXRD in FIG. 1 (signals see also Table 1).

The structure was solved to give the crystallographical parameters reported in Table 2. The single crystal structure of Complex I was determined at −170° C. The crystal structure of the crystalline complex of 4-hydroxybenzoic acid and pyrachlostrobin has a triclinic crystal system and the space group is P-1. The crystallographical parameters are reported in table 2.

Studies of single crystals of the crystalline complex of 4-hydroxybenzoic acid and pyraclostrobin show that the crystal system is triclinic and has the space group P-1. The structure analysis reveals that the crystalline complex is a 1:1 mixture of 4-hydroxybenzoic acid and pyraclostrobin with the asymmetric unit containing one molecule of 4-hydroxybenzoic acid and pyraclostrobin, each. The spatial arrangement of the 4-hydroxybenzoic and pyraclostrobin molecules in the crystal seems to be mainly driven by hydrogen bonding in between two 4-hydroxy benzoic acid molecules and also hydrogen bonding in between 4-hydroxy benzoic acid and pyraclostrobin molecules. The characteristic data of the crystal structure of the complex are shown in table 2:

TABLE 2

Crystallographic data of the crystalline complex of 4-hydroxybenzoic acid and pyraclostrobin

| Parameter | |
| --- | --- |
| Crystal system | Triclinic |
| Space group | P-1 |
| a | 8.200(1) Å |
| b | 11.942(2) Å |
| c | 13.626(2) Å |
| α | 68.474(5)° |
| β | 87.962(6)° |
| γ | 80.097(6)° |
| Volume | 1222.3(2) Å$^3$ |
| Z | 2 |
| Density (calculated) | 1.43 g/cm$^3$ |
| R-Factor (%) | 3.59 | a, b, c = Length of the edges of the unit cell
α, β, γ = Angles of the unit cell
Z = Number of molecules, in the unit cell

Example 3

Complex II

For a 1:1 co-crystal of epoxiconazol and 4-hydroxi benzoic acid, 250.0 mg of pyraclostrobin, 104.7 mg of 4-hydroxi benzoic acid and 100 µl of 50 v/v-% water-acetonitrile solution was grinded in a ball mill (Retsch Modell MM301) for 20 minutes. The residual solvents were left to dry in air. The crystalline product gave the PXRD in FIG. 2 (signals see also Table 3).

Example 4

Complex II

For a 1:1 co-crystal of epoxiconazol and 4-hydroxy benzoic acid, 100 mg of epoxiconazol and 41.9 mg of 4-hydroxy benzoic acid were placed in a 10 ml glass vial and dissolved in 4 ml of acetone at 40° C. to give a clear solution. The solution was left to evaporate at RT in the open vial. After 4/5 of the solvent had evaporated, the solution was filtered. The clear needle like crystals were analyzed with PXRD (FIG. 2, table 3) and single crystal structure determination (Table 4) to be Complex 2.

TABLE 4

Crystallographic data of the crystalline complex of 4-hydroxybenzoic acid and epoxiconazol

| Parameter | |
| --- | --- |
| Crystal system | Monoclinic |
| Space group | P 2$_1$/c |
| a | 18.640(4) Å |
| b | 5.520(2) Å |
| c | 23.622(9) Å |
| α | 90° |
| β | 190.70(2)° |
| γ | 90° |
| Volume | 2111.2(2) Å$^3$ |
| Z | 4 |
| Density (calculated) | 1.43 g/cm$^3$ |
| R-Factor (%) | 3.84 | a, b, c = Length of the edges of the unit cell
α, β, γ = Angles of the Unit cell
Z = Number of molecules, in the unit cell

Example 5

Complex III

For a 1:1 co-crystal of tebuconazol and 4-hydroxy benzoic acid, 200.1 mg of tebuconazol, 80.4 mg of 4-hydroxi benzoic acid and 150 µl ethanol was grinded in a ball mill (Retsch Modell MM301) for 10 minutes by using 20 Hz. The crystalline product gave the PXRD in FIG. 3 (table 5).

Example 6

Complex IV

For a 1:1 co-crystal of boscalid and 4-hydroxy benzoic acid, 200.0 mg of boscalid, 80.4 mg of 4-hydroxi benzoic acid and 150 µl of ethanol was grinded in a ball mill (Retsch Modell MM301) for 10 minutes by using 20 Hz. The crystalline product gave the PXRD in FIG. 4 (table 6).

Example 7

Complex V

For a 1:1 co-crystal of imazethapyr and 4-hydroxy benzoic acid, 200.3 mg of imazethapyr, 95.5 mg of 4-hydroxi benzoic acid and 150 µl of ethanol was grinded in a ball mill (Retsch Modell MM301) for 10 minutes by using 20 Hz. The crystalline product gave the PXRD in FIG. 5 (table 7).

The single crystal structure of Complex V was determined at −170° C. The crystal structure of the crystalline complex of 4-hydroxybenzoic acid and imazethapyr has a monoclinic crystal system and the space group is $P2_1/n$. The crystallographical parameters are reported in table 8.

Studies of single crystals of the crystalline complex of 4-hydroxybenzoic acid and imazethapyr show that the crystal system is triclinic and has the space group $P2_1/n$. The structure analysis reveals that the crystalline complex is a 1:1 mixture of 4-hydroxybenzoic acid and imazethapyr with the asymmetric unit containing one molecule of 4-hydroxybenzoic acid and imazethapyr, each. The spatial arrangement of the 4-hydroxybenzoic and imazethapyr molecules in the crystal seems to be mainly driven by hydrogen bonding in between two 4-hydroxy benzoic acid molecules and also hydrogen bonding in between 4-hydroxy benzoic acid and imazethapyr molecules. The characteristic data of the crystal structure of the complex are shown in table 8:

TABLE 8

Crystallographic data of the crystalline complex of 4-hydroxybenzoic acid and imazethapyr

| Parameter | |
|---|---|
| Crystal system | Monoclinic |
| Space group | $P2_1/n$ |
| a | 6.7912(3) Å |
| b | 26.416(1) Å |
| c | 12.1439(6) Å |
| α | 90° |
| β | 97.007(1)° |
| γ | 90° |
| Volume | 2162.3(2) Å$^3$ |
| Z | 4 |
| Density (calculated) | 1.31 g/cm$^3$ |
| R-Factor (%) | 6.57 | a, b, c = Length of the edges of the unit cell
α, β, γ = Angles of the unit cell
Z = Number of molecules, in the unit cell Example 8

Complex VI

For a 1:1 co-crystal of imazamox and 4-hydroxy benzoic acid, 200.1 mg of imazamox, 90.4 mg of 4-hydroxi benzoic acid and 150 µl of ethanol was grinded in a ball mill (Retsch Modell MM301) for 10 minutes by using 20 Hz. The crystalline product gave the PXRD in FIG. 6.

The single crystal structure of Complex VI was determined at −170° C. The crystal structure of the crystalline complex of 4-hydroxybenzoic acid and imazamox has a monoclinic crystal system and the space group is $P2_1/n$. The crystallographical parameters are reported, in table 2.

Studies of single crystals of the crystalline complex of 4-hydroxybenzoic acid and imazamox show that the crystal system is monoclinic and has the space group $P2_1/n$. The structure analysis reveals that the crystalline complex is a 1:1 mixture of 4-hydroxybenzoic acid and imazamox with the asymmetric unit containing one molecule of 4-hydroxybenzoic acid and imazamox, each. The spatial arrangement of the 4-hydroxybenzoic and imazamox molecules in the crystal seems to be mainly driven by hydrogen bonding in between two 4-hydroxy benzoic acid molecules and also hydrogen bonding in between 4-hydroxy benzoic acid and imazamox molecules. The characteristic data of the crystal structure of the complex are shown in table 10:

TABLE 10

Crystallographic data of the crystalline complex of 4-hydroxybenzoic acid and imazamox

| Parameter | |
|---|---|
| Crystal system | Monoclinic |
| Spacegroup | $P2_1/n$ |
| a | 6.8988(4) Å |
| b | 27.803(1) Å |
| c | 11.5194(6) Å |
| α | 90° |
| β | 94.622(2)° |
| γ | 90° |
| Volume | 2202.4(2) Å$^3$ |
| Z | 4 |
| Density (calculated) | 1.34 g/cm$^3$ |
| R-Factor (%) | 12.88 | a, b, c = Length of the edges of the unit cell
α, β, γ = Angles of the unit cell
Z = Number of molecules, in the unit cell Example 9

Complex VII

For a 1:1 co-crystal of acetamiprid and 4-hydroxy benzoic acid, 222.7 mg of acetamiprid, 138.1 mg of 4-hydroxy benzoic acid and 100 µl of ethanol solution was grinded in a ball mill (Retsch Modell MM301) for 15 minutes. The residual solvents were left to dry in air. The crystalline product gave the PXRD presented in FIG. 7.

Example 10

Complex VII

For a 1:1 co-crystal of acetamiprid and 4-hydroxy benzoic acid, 222.7 mg of acetamiprid, 138.1 mg of 4-hydroxy benzoic acid were placed in a 10 ml glass vial and dissolved in 4 ml of Acetonitrile at RT to give a clear solution. The solution was left to evaporate at RT in the open vial. After all of the solvent had evaporated, one crystal was selected for single crystal structure determination. The structure was solved to give the crystallographical parameters reported in Table 12.

The single crystal structure of Complex VII was determined at −170° C. The crystal structure of the crystalline complex of 4-hydroxybenzoic acid and acetamiprid has a triclinic crystal system and the space group is P-1. The crystallographical parameters are reported in table 12.

Studies of single crystals of the crystalline complex of 4-hydroxybenzoic acid and acetamiprid show that the crystal system is triclinic and has the space group P-1. The structure analysis reveals that the crystalline complex is a 1:1 mixture of 4-hydroxybenzoic acid and pyraclostrobin with the asymmetric unit containing two independent molecules of 4-hydroxybenzoic acid and acetamiprid, each. The spatial arrangement of the 4-hydroxybenzoic and acetamiprid molecules in the crystal seems to be mainly driven by hydrogen bonding in between two 4-hydroxy benzoic acid molecules and also hydrogen bonding in between 4-hydroxy benzoic acid and acetamiprid molecules. The characteristic data of the crystal structure of the complex are shown in table 12

TABLE 12

Crystallographic data of the crystalline complex of 4-hydroxybenzoic acid and acetamiprid

| Parameter | |
|---|---|
| Crystal system | Triclinic |
| Space group | P -1 |
| a | 5.9294(3) Å |
| b | 13.1194(7) Å |
| c | 22.4526(11) Å |
| α | 78.408(2)° |
| β | 85.082(2)° |
| γ | 81.015(2)° |
| Volume | 1687.38 Å$^3$ |
| Z | 4 |
| Density (calculated) | 1.42 g/cm$^3$ |
| R-Factor (%) | 9.61 | a, b, c = Length of the edges of the unit cell
α, β, γ = Angles of the unit cell
Z = Number of molecules. in the unit cell
The crystalline Complex VII has typically a melting point in the range from 120 to 130° C., in particular in the range from 124 to 127° C.

B) Analytic of the Obtained Complexes

The X-ray powder diffractograms displayed in FIGS. 1 to 6 were recorded using a Panalytical X'Pert Pro diffractometer (manufacturer: Panalytical) in reflection geometry in the range from 2θ=3°–35° C. with increments of 0.0167° C. using Cu—Kα radiation (at 25° C. The recorded 2θ values were used to calculate the stated interplanar spacings d. The intensity of the peaks (y-axis: linear intensity counts) is plotted versus the 2θ angle (x-axis in degrees 2θ).

The single crystal X-ray diffraction data of Complex I and Complex II was collected on a Bruker AXS CCD Detector using graphite Cu—Kα radiation. The structures were solved using direct methods, refined and expanded by using Fourier techniques with SHELX software package (G. M. Sheldrick, SHELX-97, University of Gottingen, 1997). Absorption correction was performed with SADABS software.

Melting points indicated herein refer to values determined on a Mettler hot stage in combination with a light microscope and were those given in the description as set forth above.

C) DSC Measurements

DSC was performed on a Mettler Toledo DSC 822e module. Crystals coming from solution crystallization and taken from a mother liquor were dried gently on a filter paper and laced in crimped but vented aluminium sample pans for the DSC experiments. The sample size in each case was 5 to 10 mg. The starting temperature was in each measurement 30° C., but the end temperature varied from case to case, but was typically below 200° C. The heating rate was 5° C./min. The samples were purged with a stream of nitrogen flowing at 150 ml/min for the DSC experiment.

Complex I:
The DSC-measurement with a heating rate of 5° C./min of the crystalline complex of 4-hydroxybenzoic acid and pyraclostrobin shows an endothermic melting peak with onset at 115.7° C. and peak maximum at 119° C. The melting point of the crystalline complex is thus ~50° C. higher than the melting point of pyraclostrobin (66° C.).

Complex II:
The DSC-measurement with a heating rate of 5° C./min of the crystalline complex of 4-hydroxybenzoic acid and epoxiconazol shows an endothermic melting peak with onset at 153.9° C. and peak maximum at 155° C. Melting point of the epoxiconazol is 136° C.

Complex III:
The DSC-measurement with a heating rate of 5° C./min of the crystalline complex of 4-hydroxybenzoic acid and tebuconazol shows an endothermic melting peak with onset at 148.2° C. and peak maximum at 148.9° C. The melting point of the crystalline complex is thus ~40-50° C. higher than the melting point of tebuconazol (96-104° C.).

Complex VI:
The DSC-measurement with a heating rate of 5° C./min of the crystalline complex of 4-hydroxybenzoic acid and imazamox shows an endothermic melting peak with onset at 148.2° C. and peak maximum at 148.9° C. Melting point of imazamox alone is 166° C.

Complex VII:
The DSC-measurement with a heating rate of 5° C./min of the crystalline complex of 4-hydroxybenzoic acid and acetamiprid shows an endothermic melting peak with onset at 125.2 C and peak maximum at 126.1° C. Melting point of Acetamprid is 99° C.

D) Solubility the Determination of the Amount of the Actives in Solution was Performed on HPLC ACQUITY (Water) system, equipped with PDA__230 nm UV detector and Sample Manager auto injector. Waters' Enpower software was used to record the chromatograms and to calculate the chromatographic parameters. Gradient elution (ACN—0.1% H3PO4) was achieved using C18 column, 50×2, 1 mm, 1.7 µm BEH. Injection volume was set 1 µL by auto injector. The analysis were performed with rate flux of 0.4 ml/min. UV detection was performed at 200 nm (for imazethapyr and for complex V) or 245 nm (for acetamiprid and for complex VII). Peak identities were confirmed by spectrum and retention time comparison. All the analysis were performed at room temperature. All the analyzed solutions were prepared by slurry equilibration experiments. Particularly, water suspensions of imazethapyr, acetamiprid and of the corresponding complexes V and VII were slurried for 24 hours, according with the maximum value of the intrinsic dissolution profile of the pure active. The suspensions were filtered and both solid phase and liquid phase were analyzed by XRPD and HPLC, respectively.

The solubility of the crystalline complex V in water is typically lower, if compared to the crystalline imazethapyr alone. In particular complex V has a water solubility value at room temperature of 480 mg/l, while this value for crystalline imazethapyr is 1030 mg/I. This value corresponds to the solubility of the crystalline material in water at a pH value due to the pKa of the compound itself.

The solubility of the crystalline Complex VII in water is lower, if compared to the crystalline acatamiprid alone. In particular complex VII has a water solubility value at room temperature of 1890 mg/l, while this value for crystalline acetamiprid is 2750 mg/I. This value corresponds to the solubility of the crystalline material in water at a pH value due to the pKa of the compound itself.

F)—Germination Rate
F-1) production FS Acetamiprid-solo: To 296 g water were added 44 g Acetamiprid, 7 g Atlas G-5000 and 14 g 1,2-Propyleneglykol. The mixture was milled on a Cavitron mechanical mill for 2 hours at 15° C. Then a DSC measurement was performed on a sub-sample, confirming an unchanged melting peak at 99° C., the melting point of Acetamprid. The mixture was then bead-milled for 5 hours on a Dispermat beadmill. Finally, 151 g of the bead-milled suspension were completed with 43 g water and 21 g of a 2%-xanthan-gum-solution to arrive at a white suspension that contains 75 g/L Acetamiprid.

F-2) production FS Acetamiprid-cocrystal: To 753 g water were added 125 g acetamiprid, 79 g 4-hydroxybenzoic acid, 13 g Atlas G-5000 and 40 g 1,2-propyleneglykol. The mixture was milled on a Cavitron mechanical mill for 2 hours at 50° C. Then a DSC measurement was performed on a sub-sample, showing a melting peak at 127° C., indicating that Acetamiprid has been transformed into a cocrystal. The mixture was then bead-milled for 5 hours on a Dispermat beadmill. Finally, 143 g of the bead-milled suspension were completed with 53 g water and 21 g of a 2%-xanthan-gum-solution to arrive at a white suspension that contains 75 g/L acetamiprid.

F-3) production FS pyraclostrobin-solo: To 1080 g water were added 146 g pyraclostrobin, 13 g Atlas G-5000 and 40 g 1,2-propyleneglykol. The mixture was milled at 15° C. first on a Cavitron mechanical mill and subsequently on a Dispermat beadmill. Finally, 143 g of this suspension were completed with 98 g water and 26 g of a 2%-xanthan-gum-solution to arrive at a white suspension that contains 75 g/L Pyraclostrobin F-4) production FS Pyraclostrobin-cocrystal: To 1080 g water were added 168 g Pyraclostrobin, 61 g 4-hydroxybenzoic acid, 13 g Atlas G-5000 and 40 g 1,2-Propyleneglykol. The mixture was milled on a Cavitron mechanical mill for 2 hours at 35° C. Then a DSC measurement was performed on a sub-sample, showing a melting peak at 121° C., indicating that Pyraclostrobin has been transformed into a cocrystal. The mixture was then bead-milled for 5 hours on a Dispermat beadmill. Finally, 148 g of this mixture were completed with 2 g water and 16 gram of a 2%-xanthan-gum-solution to arrive at a white suspension that contains 75 g/L pyraclostrobin.

F-5) Acetamiprid germination: In a mini-Rotostat seed-treater 2 kg OSR-seeds were treated with 4.6 g of the formulation containing acetamiprid cocrystal as described above. In a comparison 2 kg seeds were treated with 4.6 g of the formulation containing acetamiprid as pure crystals. From the treated seed batches, 100 seeds each were placed on an agar-plate. After 3 days, the number of germinated seeds treated with acetamiprid pure were compared with the number of germinated seeds treated with the acetamiprid cocrystal. Seeds treated with acetamiprid-cocrystals showed a 8% increase in germination rate.

F-6) Pyraclostrobin germination: In a mini-Rotostat seed-treater 2 kg OSR-seeds were treated with 4.6 g of the formulation containing pyraclostrobin cocrystal as described above. In a comparison 2 kg seeds were treated with 4.6 g of the formulation containing pure pyraclostrobin. From the treated seed batches, 100 seeds each were placed on an agar-plate. After 3 days, the number of germinated seeds treated with pyraclostrobin pure were compared with the number of germinated seeds treated with the pyraclostrobin cocrystal. Seeds treated with pyraclostrobin-cocrystals showed a 8% increase in germination rate.

The invention claimed is:

1. A crystalline complex of a pesticide and a co-former, wherein the pesticide is selected from the group consisting of pyraclostrobin, epoxiconazole, tebuconazole, imazethapyr, imazamox, acetamiprid and boscalid, and the co-former is 4-hydroxy benzoic acid, which, in an X-ray powder diffractogram at 25° C. and Cu radiation, shows
   (i) at least five of the following diffraction lines, given as $2\theta$ values: $6.98\pm0.2°$, $8.02\pm0.2°$, $8.46\pm0.2°$, $10.82\pm0.2°$, $12.24\pm0.2°$, $12.66\pm0.2°$, $13.23\pm0.2°$, $14.93\pm0.2°$, $16.80\pm0.2°$, $17.64\pm0.2°$, $18.74\pm0.2°$, $21.40\pm0.2°$, $23.09\pm0.2°$, $25.42\pm0.2°$, $26.33\pm0.2°$ for the crystalline complex of 4-hydroxy benzoic acid and pyraclostrobin;
   (ii) at least five of the following diffraction lines, given as $2\theta$ values: $7.50\pm0.2°$, $8.59\pm0.2°$, $9.86\pm0.2°$, $14.96\pm0.2°$, $16.51\pm0.2°$, $16.99\pm0.2°$, $19.82\pm0.2°$, $21.91\pm0.2°$, $25.52\pm0.2°$, $28.80\pm0.2°$ and $30.47\pm0.2°$ for the crystalline complex of 4-hydroxy benzoic acid and epoxiconazole;
   (iii) at least five of the following diffraction lines, given as $2\theta$ values: $6.19\pm0.2°$, $8.88\pm0.2°$, $14.51\pm0.2°$, $15.41\pm0.2°$, $16.39\pm0.2°$, $16.48\pm0.2°$, $20.15\pm0.2°$, $22.19\pm0.2°$, $26.08\pm0.2°$, $27.64\pm0.2°$ and $32.20\pm0.2°$ for the crystalline complex of 4-hydroxy benzoic acid and tebuconazole;
   (iv) at least five of the following diffraction lines, given as $2\theta$ values: $8.38\pm0.2°$, $10.15\pm0.2°$, $10.65\pm0.2°$, $11.92\pm0.2°$, $15.53\pm0.2°$, $16.39\pm0.2°$, $17.84\pm0.2°$, $18.70\pm0.2°$, $21.85\pm0.2°$, $22.41\pm0.2°$, $26.75\pm0.2°$ and $32.34\pm0.2°$ for the crystalline complex of 4-hydroxy benzoic acid and boscalid;
   (v) at least five of the following diffraction lines, given as $2\theta$ values: $6.76\pm0.2°$, $7.98\pm0.2°$, $12.39\pm0.2°$, $14.82\pm0.2°$, $15.73\pm0.2°$, $16.06\pm0.2°$, $20.92\pm0.2°$, $22.70\pm0.2°$, $26.71\pm0.2°$ and $30.74\pm0.2°$ for the crystalline complex of 4-hydroxy benzoic acid and imazethapyr;
   (vi) at least five of the following diffraction lines, given as $2\theta$ values: $6.44\pm0.2°$, $8.21\pm0.2°\pm0.2°$, $12.20\pm0.2°$, $14.48\pm0.2°$, $15.39\pm0.2°$, $15.84\pm0.2°$, $17.33\pm0.2°$, $21.02\pm0.2°$, $23.54\pm0.2°$, $24.61\pm0.2°$, $27.16\pm0.2°$ and $31.85\pm0.2°$ for the crystalline complex of 4-hydroxy benzoic acid and imazamox; or
   (vii) at least five of the following diffraction lines, given as $2\theta$ values: $7.33\pm0.2°$, $8.00\pm0.2°$, $8.73\pm0.2°$, $15.74\pm0.2°$, $16.44\pm0.2°$, $18.96\pm0.2°$, $21.93\pm0.2°$, $24.09\pm0.2°$, $25.21\pm0.2°$, $25.89\pm0.2°$, for the crystalline complex of 4-hydroxy benzoic acid and acetamiprid.

2. The crystalline complex according to claim 1, wherein
   a) the molar ratio of 4-hydroxy benzoic acid and pyraclostrobin is from 2:1 to 1:2;
   b) the molar ratio of 4-hydroxy benzoic acid and epoxiconazole is 2:1 to 1:2;
   c) the molar ratio of 4-hydroxy benzoic acid and tebuconazole is from 2:1 to 1:2,
   d) the molar ratio of 4-hydroxy benzoic acid and imazethapyr is from 2:1 to 1:2,
   e) the molar ratio of 4-hydroxy benzoic acid and imazamox is from 2:1 to 1:2;
   f) the molar ratio of 4-hydroxy benzoic acid and boscalid is from 2:1 to 1:2; or
   g) the molar ratio of 4-hydroxy benzoic acid and acetamiprid is from 2:1 to 1:2.

3. A process for preparing the crystalline complex as defined in claim 1, which comprises combining 4-hydroxy benzoic acid and the pesticide in a suitable solvent.

4. The process according to claim 3, wherein shear forces are applied to the suspension containing 4-hydroxy benzoic acid and the pesticide, which is obtained by combining 4-hydroxy benzoic and pesticide in a suitable solvent.

5. An agricultural formulation comprising the crystalline complex claim 1.

6. The agricultural composition according to claim 5, wherein the formulation is an aqueous suspension concentrate, a suspo-emulsion or water dispersable granules.

7. The agricultural composition according to claim 5, additionally comprising a further pesticide.

8. The agricultural composition according to claim 7, additionally comprising formulation auxiliaries.

9. A method for controlling phytopathogenic fungi, wherein the phytopathogenic fungi, their habitat, breeding grounds, their locus or the plants to be protected against phytopathogenic fungi, the soil or plant propagation material are treated with an effective amount of the crystalline complex as defined in claim 1.

10. The method of claim 9, wherein the crystalline complex, in an X-ray powder diffractogram at 25° C. and Cu radiation, shows
   (i) at least five of the following diffraction lines, given as 2θ values: 6.98±0.2°, 8.02±0.2°, 8.46±0.2°, 10.82±0.2°, 12.24±0.2°, 12.66±0.2°, 13.23±0.2°, 14.93±0.2°, 16.80±0.2°, 17.64±0.2°, 18.74±0.2°, 21.40±0.2°, 23.09±0.2°, 25.42±0.2°, 26.33±0.2° for the crystalline complex of 4-hydroxy benzoic acid and pyraclostrobin;
   (ii) at least five of the following diffraction lines, given as 2θ values: 7.50±0.2°, 8.59±0.2°, 9.86±0.2°, 14.96±0.2°, 16.51±0.2°, 16.99±0.2°, 19.82±0.2°, 21.91±0.2°, 25.52±0.2°, 28.80±0.2° and 30.47±0.2° for the crystalline complex of 4-hydroxy benzoic acid and epoxiconazole;
   (iii) at least five of the following diffraction lines, given as 2θ values: 6.19±0.2°, 8.88±0.2°, 14.51±0.2°, 15.41±0.2°, 16.39±0.2°, 16.48±0.2°, 20.15±0.2°, 22.19±0.2°, 26.08±0.2°, 27.64±0.2° and 32.20±0.2° for the crystalline complex of 4-hydroxy benzoic acid and tebuconazole;
   (iv) at least five of the following diffraction lines, given as 2θ values: 8.38±0.2°, 10.15±0.2°, 10.65±0.2°, 11.92±0.2°, 15.53±0.2°, 16.39±0.2% 17.84±0.2°, 18.70±0.2°, 21.85±0.2°, 22.41±0.2°, 26.75±0.2° and 32,34±0.2° for the crystalline complex of 4-hydroxy benzoic acid and boscalid;
   (v) at least five of the following diffraction lines, given as 2θ values: 6.76±0.2°, 7.98±0.2°, 12.39±0.2°, 14.82±0.2°, 15.73±0.2°, 16.06±0.2°, 20.92±0.2°, 22.70±0.2°, 26.71±0.2° and 30.74±0.2° for the crystalline complex of 4-hydroxy benzoic acid and imazethapyr;
   (vi) at least five of the following diffraction lines, given as 2θ values: 6.44±0.2°, 8.21±0.2°±0.2°, 12.20±0.2°, 14.48±0.2°, 15.39±0.2°, 15.84±0.2°, 17.33±0.2°, 21.02±0.2°, 23.54±0.2°, 24.61±0.2°, 27.16±0.2° and 31.85±0.2° for the crystalline complex of 4-hydroxy benzoic acid and imazamox; or
   (vii) at least five of the following diffraction lines, given as 2θ values: 7.33±0.2°, 8.00±0.2°, 8.73±0.2°, 15.74±0.2°, 16.44±0.2°, 18.96±0.2°, 21.93±0.2°, 24.09±0.2°, 25.21±0.2°, 25.89±0.2°, for the crystalline complex of 4-hydroxy benzoic acid and acetamiprid.

11. A method for improving the health of plants, wherein the plant, the locus where the plant is growing or is expected to grow or plant propagation material from which the plant grows is treated with an effective amount of the crystalline complex as defined in claim 1.

12. The method of claim 9, wherein the crystalline complex, in an X-ray powder diffractogram at 25° C. and Cu radiation, shows
   (i) at least five of the following diffraction lines, given as 2θ values: 6.98±0.2°, 8.02±0.2°, 8.46±0.2°, 10.82±0.2°, 12.24±0.2°, 12.66±0.2°, 13.23±0.2°, 14.93±0.2°, 16.80±0.2°, 17.64±0.2°, 18.74±0.2°, 21.40±0.2°, 23.09±0.2°, 25.42±0.2°, 26.33±0.2° for the crystalline complex of 4-hydroxy benzoic acid and pyraclostrobin;
   (ii) at least five of the following diffraction lines, given as 2θ values: 7.50±0.2°, 8.59±0.2°, 9.86±0.2°, 14.96±0.2°, 16.51±0.2°, 16.99±0.2°, 19.82±0.2°, 21.91±0.2°, 25.52±0.2°, 28.80±0.2° and 30.47±0.2° for the crystalline complex of 4-hydroxy benzoic acid and epoxiconazole;
   (iii) at least five of the following diffraction lines, given as 2θ values: 6.19±0.2°, 8.88±0.2°, 14.51±0.2°, 15.41±0.2°, 16.39±0.2°, 16.48±0.2°, 20.15±0.2°, 22.19±0.2°, 26.08±0.2°, 27.64±0.2° and 32.20±0.2° for the crystalline complex of 4-hydroxy benzoic acid and tebuconazole;
   (iv) at least five of the following diffraction lines, given as 2θ values: 8.38±0.2°, 10.15±0.2°, 10.65±0.2°, 11.92±0.2°, 15.53±0.2°, 16.39±0.2°, 17.84±0.2°, 18.70±0.2°, 21.85±0.2°, 22.41±0.2°, 26.75±0.2° and 32,34±0.2° for the crystalline complex of 4-hydroxy benzoic acid and boscalid;
   (v) at least five of the following diffraction lines, given as 2θ values: 6.76±0.2°, 7.98±0.2°, 12.39±0.2°, 14.82±0.2°, 15.73±0.2°, 16.06±0.2°, 20.92±0.2°, 22.70±0.2°, 26.71±0.2° and 30.74±0.2° for the crystalline complex of 4-hydroxy benzoic acid and imazethapyr;
   (vi) at least five of the following diffraction lines, given as 2θ values: 6.44±0.2°, 8.21±0.2°±0.2°, 12.20±0.2°, 14.48±0.2°, 15.39±0.2°, 15.84±0.2°, 17.33±0.2°, 21.02±0.2°, 23.54±0.2°, 24.61±0.2°, 27.16±0.2° and 31.85±0.2° for the crystalline complex of 4-hydroxy benzoic acid and imazamox; or
   (vii) at least five of the following diffraction lines, given as 2θ values: 7.33±0.2°, 8.00±0.2°, 8.73±0.2°, 15.74±0.2°, 16.44±0.2°, 18.96±0.2°, 21.93±0.2°, 24.09±0.2°, 25.21±0.2°, 25.89±0.2°, for the crystalline complex of 4-hydroxy benzoic acid and acetamiprid.

13. A method for protection of plant propagation material from pests comprising contacting the plant propagation materials with an effective amount of the crystalline complex as defined in claim 1.

14. The method of claim 13, wherein the crystalline complex, in an X-ray powder diffractogram at 25° C. and Cu radiation, shows
   (i) at least five of the following diffraction lines, given as 2θ values: 6.98±0.2°, 8.02±0.2°, 8.46±0.2°, 10.82±0.2°, 12.24±0.2°, 12.66±0.2°, 13.23±0.2°, 14.93±0.2°, 16.80±0.2°, 17.64±0.2°, 18.74±0.2°, 21.40±0.2°, 23.09±0.2°, 25.42±0.2°, 26.33±0.2° for the crystalline complex of 4-hydroxy benzoic acid and pyraclostrobin;
   (ii) at least five of the following diffraction lines, given as 2θ values: 7.50±0.2°, 8.59±0.2°, 9.86±0.2°, 14.96±0.2°, 16.51±0.2°, 16.99±0.2°, 19.82±0.2°, 21.91±0.2°, 25.52±0.2°, 28.80±0.2° and 30.47±0.2° for the crystalline complex of 4-hydroxy benzoic acid and epoxiconazole;
   (iii) at least five of the following diffraction lines, given as 2θ values: 6.19±0.2°, 8.88±0.2°, 14.51±0.2°, 15.41±0.2°, 16.39±0.2°, 16.48±0.2°, 20.15±0.2°, 22.19±0.2°, 26.08±0.2°, 27.64±0.2° and 32.20±0.2° for the crystalline complex of 4-hydroxy benzoic acid and tebuconazole;
   (iv) at least five of the following diffraction lines, given as 2θ values: 8.38±0.2°, 10.15±0.2°, 10.65±0.2°, 11.92±0.2°, 15.53±0.2°, 16.39±0.2°, 17.84±0.2°, 18.70±0.2°, 21.85±0.2°, 22.41±0.2°, 26.75±0.2° and 32,34±0.2° for the crystalline complex of 4-hydroxy benzoic acid and boscalid;

(v) at least five of the following diffraction lines, given as 2θ values: 6.76±0.2°, 7.98±0.2°, 12.39±0.2°, 14.82±0.2°, 15.73±0.2°, 16.06±0.2°, 20.92±0.2°, 22.70±0.2°, 26.71±0.2° and 30.74±0.2° for the crystalline complex of 4-hydroxy benzoic acid and imazethapyr;

(vi) at least five of the following diffraction lines, given as 2θ values: 6.44±0.2°, 8.21±0.2°±0.2°, 12.20±0.2°, 14.48±0.2°, 15.39±0.2°, 15.84±0.2°, 17.33±0.2°, 21.02±0.2°, 23.54±0.2°, 24, 61±0.2°, 27.16±0.2° and 31.85±0.2° for the crystalline complex of 4-hydroxy benzoic acid and imazamox; or (vii) at least five of the following diffraction lines, given as 2θ values: 7.33±0.2°, 8.00±0.2°, 8.73±0.2°, 15.74±0.2°, 16.44±0.2°, 18.96±0.2°, 21.93±0.2°, 24.09±0.2°, 25.21±0.2°, 25.89±0.2°, for the crystalline complex of 4-hydroxy benzoic acid and acetamiprid.

15. The method as claimed in claim 14, wherein the crystalline complex is applied in an amount of from 0.01 g to 10 kg per 100 kg of plant propagation materials.

16. A method for regulating the growth of plants and/or for controlling unwanted vegetation, which comprises treating plant propagation material with an effective amount of the crystalline of claim 1.

17. The method of claim 16, wherein the crystalline complex, in an X-ray powder diffractogram at 25° C. and Cu radiation, shows
   (i) at least five of the following diffraction lines, given as 2θ values: 6.76±0.2°, 7.98±0.2°, 12.39±0.2°, 14.82±0.2°, 15.73±0.2°, 16.06±0.2°, 20.92±0.2°, 22.70±0.2°, 26.71±0.2° and 30.74±0.2° for the crystalline complex of 4-hydroxy benzoic acid and imazethapyr; or
   (ii) at least five of the following diffraction lines, given as 2θ values: 6.44±0.2°, 8.21±0.2°±0.2°, 12.20±0.2°, 14.48±0.2°, 15.39±0.2°, 15.84±0.2°, 17.33±0.2°, 21.02±0.2°, 23.54±0.2°, 24.61±0.2°, 27.16±0.2° and 31.85±0.2° for the crystalline complex of 4-hydroxy benzoic acid and imazamox.

18. Plant propagation material treated with the crystalline complex as defined in claim 1 in an amount of from 0.01 g to 10 kg per 100 kg of plant propagation materials.

* * * * *